(12) United States Patent
Macari et al.

(10) Patent No.: US 12,709,740 B2
(45) Date of Patent: Aug. 18, 2026

(54) METHOD FOR HYPOTHERMIC TRANSPORT OF BIOLOGICAL SAMPLES

(71) Applicant: Paragonix Technologies, Inc., Waltham, MA (US)

(72) Inventors: Danny Macari, Sudbury, MA (US); Matthew Whitney, Upton, MA (US); Samantha Estrella, Sturbridge, MA (US); William Lucas Churchill, Braintree, MA (US)

(73) Assignee: Paragonix Technologies, Inc., Waltham, MA (US)

( * ) Notice: Subject to any disclaimer, the term of this patent is extended or adjusted under 35 U.S.C. 154(b) by 0 days.

(21) Appl. No.: 19/322,102

(22) Filed: Sep. 8, 2025

(65) Prior Publication Data

US 2025/0388872 A1 Dec. 25, 2025

Related U.S. Application Data

(63) Continuation of application No. 19/041,796, filed on Jan. 30, 2025, now Pat. No. 12,410,408.

(60) Provisional application No. 63/727,110, filed on Dec. 2, 2024, provisional application No. 63/549,145, filed on Feb. 2, 2024.

(51) Int. Cl.
*A01N 1/143* (2025.01)
*C12N 5/00* (2006.01)

(52) U.S. Cl.
CPC ............ *C12N 5/562* (2025.01); *A01N 1/143* (2025.01); *C12N 5/545* (2025.01)

(58) Field of Classification Search
CPC ................................ A01N 1/143; A01N 1/146
See application file for complete search history.

(56) References Cited

U.S. PATENT DOCUMENTS 3,323,872 A 6/1967 Scott
3,398,743 A 8/1968 Shalit
3,607,646 A 9/1971 de Roissart
3,935,065 A 1/1976 Doerig
4,336,248 A 6/1982 Bonhard et al.
4,502,295 A 3/1985 Toldeo-Pereyra
4,575,498 A 3/1986 Holmes et al.
4,643,713 A 2/1987 Viitala (Continued)

FOREIGN PATENT DOCUMENTS

CA 2980782 11/2007
CA 2722615 10/2009

(Continued)

OTHER PUBLICATIONS

Briceno et al., "Back-table surgery pancreas allograft for transplantation: Implications in complications", World Journal of Transplantation, vol. 11(1):1-6 (2021).

(Continued)

*Primary Examiner* — Jonathan M Hurst
(74) *Attorney, Agent, or Firm* — Knobbe Martens Olson & Bear, LLP

(57) ABSTRACT

A method for transporting a biological sample at hypothermic temperatures. The container can be cooled using phase change material and pump fluid through the sample. The fluid can pump through the system at a rate independent of the parameters of the biological sample. A valve can control the rate of flow of the fluid into the biological sample.

20 Claims, 20 Drawing Sheets

(56) References Cited

U.S. PATENT DOCUMENTS

| | | | | |
|---|---|---|---|---|
| 4,723,974 | A | 2/1988 | Ammerman | |
| 4,931,333 | A | 6/1990 | Henry | |
| 4,952,409 | A | 8/1990 | Bando et al. | |
| 4,976,708 | A | 12/1990 | Oshiyama | |
| 5,051,352 | A * | 9/1991 | Martindale | A01N 1/10 435/1.2 |
| 5,066,578 | A | 11/1991 | Wikman-Coffelt | |
| 5,093,969 | A | 3/1992 | McGuire | |
| 5,133,470 | A | 7/1992 | Abrams et al. | |
| 5,141,847 | A | 8/1992 | Sugimachi et al. | |
| 5,149,321 | A | 9/1992 | Klatz et al. | |
| 5,157,930 | A | 10/1992 | McGhee et al. | |
| 5,186,431 | A | 2/1993 | Tamari | |
| 5,234,405 | A | 8/1993 | Klatz et al. | |
| RE34,387 | E | 9/1993 | Holmes et al. | |
| 5,252,537 | A | 10/1993 | De Winter-Scailteur | |
| 5,285,657 | A | 2/1994 | Bacchi et al. | |
| 5,306,711 | A | 4/1994 | Andrews | |
| D347,894 | S | 6/1994 | Hansen et al. | |
| 5,320,846 | A | 6/1994 | Bistrian et al. | |
| 5,326,706 | A | 7/1994 | Yland et al. | |
| 5,356,771 | A | 10/1994 | O'Dell | |
| 5,362,622 | A | 11/1994 | O'Dell et al. | |
| 5,385,821 | A | 1/1995 | O'Dell et al. | |
| 5,395,314 | A | 3/1995 | Klatz et al. | |
| 5,434,045 | A | 7/1995 | Jost | |
| 5,435,142 | A | 7/1995 | Silber | |
| 5,570,588 | A | 11/1996 | Lowe | |
| 5,584,804 | A | 12/1996 | Klatz et al. | |
| 5,586,438 | A | 12/1996 | Fahy | |
| 5,599,659 | A | 2/1997 | Brasile et al. | |
| 5,601,972 | A | 2/1997 | Meryman | |
| 5,629,145 | A | 5/1997 | Meryman | |
| 5,643,712 | A | 7/1997 | Brasile | |
| 5,656,154 | A | 8/1997 | Meryman | |
| 5,696,152 | A | 12/1997 | Southard | |
| 5,699,793 | A | 12/1997 | Brasile | |
| 5,702,881 | A | 12/1997 | Brasile et al. | |
| 5,707,971 | A | 1/1998 | Fahy | |
| 5,709,654 | A | 1/1998 | Klatz et al. | |
| 5,712,084 | A | 1/1998 | Osgood | |
| 5,716,378 | A | 2/1998 | Minten | |
| 5,752,929 | A | 5/1998 | Klatz et al. | |
| 5,827,222 | A | 10/1998 | Klatz et al. | |
| 5,843,024 | A | 12/1998 | Brasile | |
| 5,916,800 | A | 6/1999 | Elizondo et al. | |
| 5,922,598 | A | 7/1999 | Mintchev | |
| 5,963,335 | A | 10/1999 | Boutelle | |
| 5,965,433 | A | 10/1999 | Gardetto et al. | |
| 6,014,864 | A | 1/2000 | Owen | |
| 6,020,575 | A | 2/2000 | Nagle et al. | |
| 6,024,698 | A | 2/2000 | Brasile | |
| 6,042,559 | A | 3/2000 | Dobak, III | |
| 6,046,046 | A | 4/2000 | Hassanein | |
| 6,060,232 | A | 5/2000 | Von Baeyer et al. | |
| 6,100,082 | A | 8/2000 | Hassanein | |
| 6,174,719 | B1 | 1/2001 | Elizondo et al. | |
| 6,194,137 | B1 | 2/2001 | Khirabadi et al. | |
| 6,209,343 | B1 | 4/2001 | Owen | |
| 6,241,945 | B1 | 6/2001 | Owen | |
| 6,260,360 | B1 | 7/2001 | Wheeler | |
| 6,280,925 | B1 | 8/2001 | Brockbank | |
| 6,303,388 | B1 | 10/2001 | Fahy | |
| D453,828 | S | 2/2002 | Brassil et al. | |
| 6,375,613 | B1 | 4/2002 | Brasile | |
| 6,381,981 | B1 | 5/2002 | Yaddgo et al. | |
| 6,406,839 | B1 | 6/2002 | Segall et al. | |
| 6,413,713 | B1 | 7/2002 | Serebrennikov | |
| 6,475,716 | B1 | 11/2002 | Seki | |
| 6,485,450 | B1 | 11/2002 | Owen | |
| 6,492,103 | B1 | 12/2002 | Taylor | |
| D468,436 | S | 1/2003 | Brassil et al. | |
| D470,594 | S | 2/2003 | Brassil et al. | |
| 6,569,615 | B1 | 5/2003 | Thatte et al. | |
| 6,582,953 | B2 | 6/2003 | Brasile | |
| 6,596,531 | B2 | 7/2003 | Campbell et al. | |
| 6,642,019 | B1 | 11/2003 | Anderson et al. | |
| 6,642,045 | B1 | 11/2003 | Brasile | |
| 6,656,380 | B2 | 12/2003 | Wood et al. | |
| 6,673,008 | B1 | 1/2004 | Thompson et al. | |
| 6,673,594 | B1 * | 1/2004 | Owen | A01N 1/143 435/284.1 |
| 6,677,150 | B2 | 1/2004 | Alford et al. | |
| 6,699,231 | B1 | 3/2004 | Sterman et al. | |
| 6,736,836 | B2 | 5/2004 | Montgomery | |
| 6,740,484 | B1 | 5/2004 | Khirabadi et al. | |
| 6,773,877 | B2 | 8/2004 | Fahy | |
| 6,794,124 | B2 | 9/2004 | Steen | |
| 6,794,182 | B2 | 9/2004 | Wolf, Jr. | |
| 6,905,871 | B1 | 6/2005 | Doorschodt et al. | |
| 6,924,267 | B2 | 8/2005 | Daemen et al. | |
| 6,948,334 | B1 | 9/2005 | Challenger | |
| 6,953,655 | B1 | 10/2005 | Hassanein et al. | |
| 6,977,140 | B1 | 12/2005 | Owen et al. | |
| 6,994,954 | B2 | 2/2006 | Taylor | |
| 6,997,688 | B1 | 2/2006 | Klein et al. | |
| 7,005,253 | B2 | 2/2006 | Polyak et al. | |
| 7,008,535 | B1 | 3/2006 | Spears et al. | |
| 7,029,839 | B2 | 4/2006 | Toledo-Pereyra et al. | |
| D527,225 | S | 8/2006 | Krieger et al. | |
| D531,319 | S | 10/2006 | Schein et al. | |
| D531,320 | S | 10/2006 | Garland et al. | |
| 7,157,222 | B2 | 1/2007 | Khirabadi et al. | |
| 7,176,015 | B2 | 2/2007 | Alford et al. | |
| 7,240,513 | B1 | 7/2007 | Conforti | |
| 7,270,946 | B2 | 9/2007 | Brockbank et al. | |
| 7,294,278 | B2 | 11/2007 | Spears et al. | |
| 7,316,922 | B2 | 1/2008 | Streeter | |
| 7,326,564 | B2 | 2/2008 | Lundell et al. | |
| 7,361,365 | B2 | 4/2008 | Birkett et al. | |
| 7,410,474 | B1 | 8/2008 | Friend et al. | |
| D576,488 | S | 9/2008 | Miota et al. | |
| 7,504,201 | B2 | 3/2009 | Taylor et al. | |
| 7,572,622 | B2 | 8/2009 | Hassanein et al. | |
| 7,651,835 | B2 | 1/2010 | Hassanein et al. | |
| 7,678,563 | B2 | 3/2010 | Wright et al. | |
| 7,691,622 | B2 | 4/2010 | Garland et al. | |
| 7,749,693 | B2 | 7/2010 | Brassil et al. | |
| 7,811,808 | B2 | 10/2010 | van der Plaats et al. | |
| 7,824,848 | B2 | 11/2010 | Owen et al. | |
| D630,318 | S | 1/2011 | Goodwin | |
| 7,897,327 | B2 | 3/2011 | Millis et al. | |
| 8,097,449 | B2 | 1/2012 | Garland et al. | |
| 8,152,367 | B2 | 4/2012 | Roberts et al. | |
| D664,261 | S | 7/2012 | Kravitz et al. | |
| 8,268,547 | B2 | 9/2012 | Owen et al. | |
| 8,268,612 | B2 | 9/2012 | Owen et al. | |
| 8,304,181 | B2 | 11/2012 | Hassanein et al. | |
| D672,466 | S | 12/2012 | Kravitz et al. | |
| 8,323,954 | B2 | 12/2012 | Kravitz et al. | |
| 8,361,091 | B2 | 1/2013 | Schein et al. | |
| 8,420,380 | B2 | 4/2013 | Fishman et al. | |
| 8,465,970 | B2 | 6/2013 | Hassanein et al. | |
| D692,159 | S | 10/2013 | Judson et al. | |
| D692,160 | S | 10/2013 | Judson et al. | |
| 8,613,202 | B2 | 12/2013 | Williams | |
| D697,224 | S | 1/2014 | Judson et al. | |
| 8,685,709 | B2 | 4/2014 | Bunegin et al. | |
| 8,785,116 | B2 | 7/2014 | Anderson et al. | |
| 8,802,425 | B2 | 8/2014 | Ferrera | |
| D713,972 | S | 9/2014 | Judson et al. | |
| D714,461 | S | 9/2014 | Judson et al. | |
| D714,462 | S | 9/2014 | Judson et al. | |
| 8,828,034 | B2 | 9/2014 | Kravitz et al. | |
| 8,828,710 | B2 | 9/2014 | Anderson et al. | |
| 8,835,158 | B2 | 9/2014 | Judson et al. | |
| D727,492 | S | 4/2015 | Scampoli | |
| D734,868 | S | 7/2015 | Gilboa | |
| 9,089,126 | B2 | 7/2015 | Faulkner et al. | |
| 9,155,297 | B2 | 10/2015 | Anderson et al. | |
| 9,247,728 | B2 | 2/2016 | Fishman et al. | |
| 9,253,976 | B2 | 2/2016 | Anderson et al. | |
| 9,259,562 | B2 | 2/2016 | Steinman et al. | |
| 9,357,767 | B2 | 6/2016 | Steinman et al. | |

(56) References Cited

U.S. PATENT DOCUMENTS 9,426,979 B2 8/2016 Anderson et al.
D765,874 S 9/2016 Judson et al.
9,560,846 B2 2/2017 Anderson et al.
D787,696 S 5/2017 Schmieta et al.
D791,939 S 7/2017 Turturro et al.
9,867,368 B2 1/2018 Anderson et al.
9,910,000 B2 3/2018 Lynam et al.
9,936,689 B2 4/2018 Anderson et al.
D819,223 S 5/2018 Judson et al.
10,076,112 B2 9/2018 Hassanein et al.
10,085,441 B2 10/2018 Steinman et al.
D861,161 S 9/2019 Schuessler
D882,077 S 4/2020 Schmitt
D884,887 S 5/2020 Kangastupa
D901,680 S 11/2020 Guala
10,918,102 B2 2/2021 Uygun et al.
D912,245 S 3/2021 Grudo et al.
11,089,775 B2 8/2021 Anderson et al.
11,166,452 B2 11/2021 Judson et al.
11,178,866 B2 11/2021 Anderson et al.
D963,194 S 9/2022 Bixon et al.
11,472,625 B2 10/2022 Mirzaee Kakhki
11,528,903 B1 12/2022 He et al.
D975,273 S 1/2023 Theriot
11,576,371 B2 2/2023 Legallais et al.
11,632,951 B2 4/2023 Collette et al.
11,659,834 B2 5/2023 Judson et al.
D999,370 S 9/2023 Wade et al.
D1,002,868 S 10/2023 Bixon et al.
D1,003,434 S 10/2023 Fangrow
11,785,938 B2 10/2023 Clavien et al.
D1,016,251 S 2/2024 Castriotta et al.
D1,031,028 S 6/2024 Bornhoft et al.
12,035,708 B2 7/2024 Anderson et al.
12,052,985 B2 8/2024 Anderson et al.
12,070,029 B2 8/2024 Collette et al.
12,096,765 B1 9/2024 Anderson et al.
12,121,023 B1 10/2024 Anderson et al.
12,161,110 B2 12/2024 Collette et al.
12,178,206 B2 12/2024 Collette et al.
12,245,585 B2 3/2025 Judson et al.
12,245,586 B2 3/2025 Anderson et al.
12,279,610 B2 4/2025 Anderson et al.
12,310,357 B2 5/2025 Collette et al.
12,342,810 B2 7/2025 Anderson et al.
12,357,533 B2 7/2025 Bulka et al.
12,369,576 B2 7/2025 Anderson et al.
D1,087,382 S 8/2025 Macari et al.
12,410,408 B2 9/2025 Macari et al.
12,485,064 B2 12/2025 Bulka et al.
12,543,729 B2 2/2026 Anderson et al.
2001/0025191 A1 9/2001 Montgomery
2002/0042131 A1 4/2002 Brockbank et al.
2002/0051779 A1 5/2002 Gage et al.
2002/0064768 A1 5/2002 Polyak et al.
2002/0068360 A1 6/2002 Brockbank et al.
2002/0115634 A1 8/2002 Polyak et al.
2002/0138013 A1 9/2002 Guerrero et al.
2002/0177117 A1 11/2002 Wolf
2003/0022148 A1 1/2003 Seki
2003/0053998 A1 3/2003 Daemen et al.
2003/0054540 A1 3/2003 Alford et al.
2003/0080126 A1 5/2003 Voute et al.
2003/0118980 A1 6/2003 Taylor
2003/0125804 A1 7/2003 Kruse et al.
2003/0180704 A1 9/2003 Brockbank et al.
2004/0014199 A1 1/2004 Streeter
2004/0038192 A1 2/2004 Brasile
2004/0038193 A1 2/2004 Brasile
2004/0045314 A1 3/2004 Roth et al.
2004/0058432 A1 3/2004 Owen et al.
2004/0067480 A1 4/2004 Brockbank et al.
2004/0111104 A1 6/2004 Schein et al.
2004/0170950 A1 9/2004 Prien
2004/0171138 A1 9/2004 Hassanein et al.
2004/0221719 A1 11/2004 Wright et al.
2004/0224298 A1 11/2004 Brassil et al.
2004/0224299 A1 11/2004 Garland et al.
2004/0241634 A1 12/2004 Millis et al.
2004/0248281 A1 12/2004 Wright et al.
2005/0100876 A1 5/2005 Khirabadi et al.
2005/0147958 A1 7/2005 Hassanein et al.
2005/0153271 A1 7/2005 Wenrich
2005/0221269 A1 10/2005 Taylor et al.
2005/0233299 A1 10/2005 Sawa et al.
2005/0255442 A1 11/2005 Brassil et al.
2005/0277106 A1 12/2005 Daemen et al.
2006/0019388 A1 1/2006 Hutmacher et al.
2006/0063142 A1 3/2006 Owen et al.
2006/0121439 A1 6/2006 Baker
2006/0121512 A1 6/2006 Parenteau
2006/0121605 A1 6/2006 Parenteau
2006/0141077 A1 6/2006 Pettersson
2006/0148062 A1 7/2006 Hassanein et al.
2006/0154357 A1 7/2006 Hassanein et al.
2006/0154358 A1 7/2006 Hassanein et al.
2006/0154359 A1 7/2006 Hassanein et al.
2006/0160204 A1 7/2006 Hassanein et al.
2006/0168985 A1 8/2006 Gano
2006/0233986 A1 10/2006 Gutsche et al.
2006/0292544 A1 12/2006 Hassanein et al.
2007/0009881 A1 1/2007 Arzt et al.
2007/0015131 A1 1/2007 Arzt et al.
2007/0028642 A1 2/2007 Glade et al.
2007/0166292 A1 7/2007 Brasile
2007/0184545 A1 8/2007 Plaats et al.
2007/0190636 A1 8/2007 Hassanein et al.
2007/0193297 A1 8/2007 Wilson
2007/0243518 A1 10/2007 Sema et al.
2007/0264485 A1 11/2007 Stepanian et al.
2007/0275364 A1 11/2007 Hassanein et al.
2008/0017194 A1 1/2008 Hassanein et al.
2008/0070229 A1 3/2008 Streeter
2008/0070302 A1 3/2008 Brockbank et al.
2008/0096184 A1 4/2008 Brasile
2008/0145919 A1 6/2008 Franklin et al.
2008/0187901 A1 8/2008 Doorschodt et al.
2008/0234768 A1 9/2008 Hassanein et al.
2008/0286747 A1 11/2008 Curtis et al.
2008/0288399 A1 11/2008 Curtis et al.
2008/0311552 A1 12/2008 Min
2009/0078699 A1 3/2009 Mustafa et al.
2009/0197240 A1 8/2009 Fishman et al.
2009/0197241 A1 8/2009 Fishman et al.
2009/0197292 A1 8/2009 Fishman et al.
2009/0197324 A1 8/2009 Fishman et al.
2009/0197325 A1 8/2009 Fishman et al.
2009/0199904 A1 8/2009 Babbitt et al.
2009/0226878 A1 9/2009 Taylor et al.
2009/0240277 A1 9/2009 Connors et al.
2009/0291486 A1 11/2009 Wenrich
2010/0015592 A1 1/2010 Doorschodt
2010/0028850 A1 2/2010 Brassil
2010/0056966 A1 3/2010 Toth
2010/0086907 A1 4/2010 Bunegin et al.
2010/0112542 A1 5/2010 Wright et al.
2010/0129784 A1* 5/2010 Eichentopf .............. A01N 1/10 604/247
2010/0151559 A1 6/2010 Garland et al.
2010/0171802 A1 7/2010 Lee et al.
2010/0175393 A1 7/2010 Burke et al.
2010/0209902 A1 8/2010 Zal et al.
2010/0216110 A1 8/2010 Brockbank
2010/0221696 A1 9/2010 Owen et al.
2010/0233670 A1 9/2010 Gavish
2010/0234928 A1 9/2010 Rakhorst et al.
2011/0033916 A1* 2/2011 Hutzenlaub ............ A01N 1/148 435/284.1
2011/0039253 A1 2/2011 Owen et al.
2011/0053256 A1 3/2011 Owen et al.
2011/0059429 A1 3/2011 Owen et al.
2011/0065169 A1 3/2011 Steen et al.
2011/0129810 A1 6/2011 Owen et al.
2011/0129908 A1 6/2011 Owen et al.

(56) References Cited

U.S. PATENT DOCUMENTS

2011/0136096 A1 6/2011 Hassanein et al.
2011/0173023 A1 7/2011 LeClair et al.
2011/0177487 A1 7/2011 Simsir et al.
2011/0183310 A1 7/2011 Kravitz et al.
2011/0212431 A1 9/2011 Bunegin et al.
2011/0217689 A1 9/2011 Bunegin et al.
2012/0042976 A1 2/2012 Toledo
2012/0116152 A1 5/2012 Faulkner et al.
2012/0148542 A1 6/2012 Kravitz
2012/0264104 A1 10/2012 Ferrera
2012/0266564 A1 10/2012 Haarmann et al.
2012/0301952 A1 11/2012 Anderson et al.
2012/0309078 A1 12/2012 Anderson et al.
2013/0177897 A1 7/2013 Kravitz et al.
2014/0041403 A1 2/2014 Anderson et al.
2014/0087357 A1 3/2014 Kohl et al.
2014/0140815 A1 5/2014 Shener-Irmakoglu et al.
2014/0157797 A1 6/2014 Kovalick et al.
2014/0314881 A1 10/2014 Reynolds et al.
2014/0349273 A1 11/2014 Anderson et al.
2014/0356850 A1 12/2014 Anderson et al.
2014/0356933 A1 12/2014 Anderson et al.
2014/0377880 A1 12/2014 Emburgh et al.
2015/0204598 A1 7/2015 Affleck et al.
2015/0209017 A1 7/2015 Fleming et al.
2015/0230453 A1 8/2015 Fontes et al.
2015/0373967 A1 12/2015 Anderson et al.
2016/0074234 A1 3/2016 Abichandani et al.
2016/0095310 A1 4/2016 Anderson et al.
2016/0183517 A1 6/2016 Potenziano
2016/0271015 A1 9/2016 Wengreen et al.
2016/0347532 A1 12/2016 McCormick
2016/0355318 A1 12/2016 Epentos et al.
2016/0362240 A1 12/2016 Ferracamo, Jr.
2016/0374332 A1 12/2016 Hassanein et al.
2017/0058257 A1 3/2017 Levner et al.
2017/0113181 A1 4/2017 Sinstedten et al.
2017/0318803 A1 11/2017 Gil et al.
2018/0000068 A1 1/2018 Peralta
2018/0132478 A1 5/2018 Anderson et al.
2018/0352807 A1 12/2018 Judson et al.
2019/0038388 A1 2/2019 Schmitt et al.
2019/0175394 A1 6/2019 Kim
2019/0320649 A1 10/2019 Bunegin
2019/0374693 A1 12/2019 Kheradvar et al.
2020/0187490 A1 6/2020 Kravitz et al.
2020/0253195 A1 8/2020 Bagnato et al.
2020/0278339 A1 9/2020 Wang et al.
2020/0375178 A1 12/2020 Becker et al.
2021/0400952 A1 12/2021 Judson et al.
2021/0400953 A1* 12/2021 Anderson ............. A01N 1/122
2022/0007368 A1 1/2022 Tang et al.
2022/0007638 A1* 1/2022 Judson .................. C12M 45/22
2022/0256838 A1 8/2022 Anderson et al.
2022/0322658 A1 10/2022 Keshavjee et al.
2023/0059208 A1 2/2023 Shelton et al.
2023/0073834 A1 3/2023 Luke
2023/0089628 A1 3/2023 Freed
2023/0092486 A1 3/2023 Pettinato et al.
2023/0284613 A1 9/2023 Filgate et al.
2023/0284614 A1 9/2023 Anderson et al.
2023/0337659 A1 10/2023 Judson et al.
2024/0389577 A1 11/2024 Anderson et al.
2025/0064052 A1 2/2025 Bulka et al.
2025/0064674 A1 2/2025 Bulka et al.
2025/0072415 A1 3/2025 Anderson et al.
2025/0072416 A1 3/2025 Anderson et al.
2025/0198984 A1 6/2025 Patel
2025/0204518 A1 6/2025 Patel
2025/0204519 A1 6/2025 Bornhoft et al.
2025/0248390 A1 8/2025 Macari et al.
2025/0311717 A1 10/2025 Churchill et al.
2025/0311718 A1 10/2025 Churchill et al.
2025/0311719 A1 10/2025 Churchill et al.
2025/0318519 A1 10/2025 Judson et al.
2025/0339335 A1 11/2025 Bulka et al.
2025/0344691 A1 11/2025 Judson et al.
2025/0344692 A1 11/2025 Collette et al.
2025/0351816 A1 11/2025 Anderson et al.
2025/0351817 A1 11/2025 Judson et al.
2025/0374918 A1 12/2025 Tajima et al.

FOREIGN PATENT DOCUMENTS

CA 2775327 3/2011
CA 3149024 3/2021
CH 551741 7/1974
CN 100402103 C 7/2008
CN 101322861 12/2008
CN 104619169 5/2015
CN 105660603 6/2016
CN 205337358 6/2016
CN 107183005 9/2017
CN 112806351 5/2021
CN 308966732 11/2024
DE 19922310 11/2000
DE 10-2005-048625 4/2007
EP 0376763 7/1990
EP 1017274 11/2003
EP 2278874 2/2011
EP 2480069 8/2012
EP 4344544 4/2024
FR 2830077 4/2004
JP H08-169801 7/1996
JP 2000-279519 10/2000
JP 3775098 5/2006
JP 2008-120713 5/2008
KR 10-1499735 3/2015
WO WO 1991/03934 4/1991
WO WO 1994/09274 4/1994
WO WO 1995/12973 5/1995
WO WO 1996/30111 10/1996
WO WO 1997/43899 11/1997
WO WO 1999/15011 4/1999
WO WO 2000/18225 4/2000
WO WO 2000/18226 4/2000
WO WO 2000/60935 10/2000
WO WO 2001/03505 1/2001
WO WO 2001/37719 5/2001
WO WO 2001/54495 8/2001
WO WO 2001/78504 10/2001
WO WO 2001/78505 10/2001
WO WO 2001/95717 12/2001
WO WO 2002/17714 3/2002
WO WO 2002/26034 4/2002
WO WO 2002/32225 4/2002
WO WO 2002/089571 11/2002
WO WO 2004/017838 3/2004
WO WO 2004/026031 4/2004
WO WO 2004/052101 6/2004
WO WO 2004/089085 10/2004
WO WO 2004/089090 10/2004
WO WO 2004/105484 12/2004
WO WO 2004/110146 12/2004
WO WO 2005/022994 3/2005
WO WO 2005/074681 8/2005
WO WO 2005/099588 10/2005
WO WO 2006/033674 3/2006
WO WO 2006/042138 4/2006
WO WO 2006/052133 5/2006
WO WO 2006/060709 6/2006
WO WO 2006/101393 9/2006
WO WO 2007/025215 3/2007
WO WO 2007/111495 10/2007
WO WO 2007/124044 11/2007
WO WO 2008/108996 9/2008
WO WO 2008/144021 11/2008
WO WO 2008/150587 12/2008
WO WO 2009/020412 2/2009
WO WO 2009/041806 4/2009
WO WO 2009/099939 8/2009
WO WO 2009/132018 10/2009
WO WO 2010/084424 7/2010
WO WO 2010/096821 8/2010

(56) References Cited

FOREIGN PATENT DOCUMENTS

| | | |
|---|---|---|
| WO | WO 2011/038251 | 3/2011 |
| WO | WO 2012/125782 | 9/2012 |
| WO | WO 2013/068752 | 5/2013 |
| WO | WO 2014/026119 | 2/2014 |
| WO | WO 2014/026128 | 2/2014 |
| WO | WO 2015/021513 | 2/2015 |
| WO | WO 2015/126853 | 8/2015 |
| WO | WO 2017/205967 | 12/2017 |
| WO | WO 2017/205987 | 12/2017 |
| WO | WO 2018/015548 | 1/2018 |
| WO | WO 2018/112072 | 6/2018 |
| WO | WO 2018/184100 | 10/2018 |
| WO | WO 2018/226993 | 12/2018 |
| WO | WO 2020/061202 | 3/2020 |
| WO | WO 2020/252148 | 12/2020 |
| WO | WO 2021/041181 | 3/2021 |
| WO | WO 2021/155147 | 8/2021 |
| WO | WO 2023/154793 | 8/2023 |
| WO | WO 2023/215611 | 11/2023 |
| WO | WO 2024/044385 | 2/2024 |
| WO | WO 2024/054588 | 3/2024 |
| WO | WO 2025/049335 | 3/2025 |
| WO | WO 2025/166189 | 7/2025 |
| WO | WO 2025/217060 | 10/2025 |
| WO | WO 2025/255395 | 12/2025 |

OTHER PUBLICATIONS

Brown, "Chemical measurements of inulin concentrations in peritoneal dialysis solution", Clin. Chim. vol. 76:103-112 (1977).

Bunegin et al., Interstitial pO2 and high energy phosphates in the canine heart during hypothermic preservation in a new, portable, pulsatile perfusion device, from the Department of Anesthesiology University of Texas Health Science Center at San Antonio, Texas; and Center for Cardiovascular Surgery of the Republic of Lithuania, Vilnius, Lithuania, vol. 3(3):1-6 (1998).

Bunegin et al., The Application of Fluidics Technology for perfusion of adult, human sized, canine hearts, from the Department of Anesthesiology, Health Science Center at San Antonio, University of Texas, vol. 8(1/2):73-78 (2003).

Bunegin et al., "The Application of Fluidics Technology for Organ Preservation", Biomedical Instrumentation & Technology, Mar./Apr. 2004, pp. 155-164.

Calhoon et al., "Twelve-Hour Canine Heart Preservation With a Simple, Portable Hypothermic Organ Perfusion Device", r\nn Thorac Surg 1996:62:91-93.

Ceulemans et al., "Combined liver and lung transplantation", American Journal of Transplantation, vol. 14(10):2412-2416 (2014).

Chi et al., "The Development of a portable ECG monitor based on DSP", Physics Procedia, vol. 33:765-774 (2012).

Cypel et al., "Extracorporeal lung perfusion", Current Opinion in Organ Transplantation, vol. 21(3):329-335 (2016).

De Perrot, "Lung preservation, Seminars in Thoracic and Cardiovascular Surgery", Saunders, Philadelphia, PA vol. 16(4):300-308 (2004).

Galasso, "Inactivating hepatits C virus in donor lungs using light therapies during normothermic ex vivo lung perfusion", Nature Communications, vol. 10(481):1-12 (2019).

Interview with CEO of Paragonix, posted at tactical-medicine.com, posting date Jul. 12, 2022, retrieved Nov. 14, 2023, online, https://tactical-medicine.com/blogs/news/improving-transplant-survival-with-organ-preservation-tech-interview-with-dr-anderson-ceo-of-paragonix (Year: 2022).

Irish Medicines Board "Viaspan" Summary of Product Characteristics available online at <https://www.hpra.ie/img/ _ ./ JcenseSPC_PA0002-075-001_21112012111041.pdf>, Nov. 21, 2012 (6 Pages).

Kidney Transport, retrieved online on Feb. 27, 2025, at: https://fluctus.nl/en/portfolio/kidney-assist/, publication date unknown.

Michel et al., "Innovative cold storage of donor organs using the Paragonix Sherpa Pak™ devices", Heart Lung and Vessels, vol. 7(3):246-255 (2015) XP093292267, retrieved from the internet on Jul. 2, 2025 at: https://pmc.ncbi.nlm.nih.gov/articles/PMC4593023/pdf/hlv-07-246.pdf.

Naoum, "Xometry: Everything you need to know about acrylic and its uses", published May 4, 2022, accessed on Jan. 14, 2025, at https://www.xometry.com/resources/materials/acrylic-pmma/#:~:text=Acrylic%20is%20a%20type%20of,worst%20and%20dysfunctional%20at%20best (2022).

Organ Recovery Systems, Inc., LifePort Brochure, www.organ-recovery.com retrieved Aug. 29, 2012 (12 pages).

Paragonix SherpaPak, posted at .mmcts.org, posting date Jun. 16, 2021, retrieved Nov. 14, 2023, online, https://mmcts.org/utuorial/1657 (Year: 2021).

Raredon et al., "Biomimetic culture reactor for whole lung engineering", BioResearch, vol. 5.1:72-83 (2016).

Steinbrook, The New England Journal of Medicine, "Organ Donation after Cardiac Death", Jul. 9, 2007 (5 pages).

T'Hart, "New solutions in organ preservation", Transplantation Reviews, vol. 16:131-141 (2006).

Tolstykh et al., "Novel portable hypothermic pulsatile perfusion preservation technology: Improved viability and function of rodent and canine kidneys", Ann Transplant, 2010; 15(3):1-9.

Tolstykh et al., "Perfusion preservation of rodent kidneys in a portable preservation device based on fuidics technology", Transplantation, vol. 73(9):1508-1526 (2002).

Vries et al., "Systms engineering the organ preservation process for transplantation", Current Opinion in Biotechnology, vol. 58:192-201 (2019).

Wandall et al., "Galactosylation does not prevent the rapid clearance of long-term 40C-stored platelets", Blood, vol. 11(6):3249-3256 (2008).

Watanabe et al., "Ex vivo lung perfusion", J Thorac Dis, vol. 13(11):6602-6617 (2021).

Weegman et al., "Continuous Real-time Viability Assessment of Kidneys Based on Oxygen Consumption", Transplant Proc. 2010; 42(6):2020-2023.

Yufer et al., "A tissue impendance measurement chip for myocardial ischemia detection", IEEE Transactions on Circuits and Systems—I:Regular Papers, vol. 52(12):2620-2628 (2005).

International Search Report and Written Opinion in application No. PCT/US2025/014071, mailed on May 21, 2025, in 38 pages.

Ma et al., "Application and research progress of phase change materials in biomedical field", Biomater. Sci. vol. 9:5762-5780 (2021).

Boteon et al., "Combined hypothermic and normothermic machine perfusion improves functional recovery of extended criteria donor livers", Liver Transplantation, vol. 24(12):1699-1715 (2018).

SamStores ("Frigidaire MFC09V4GW Chest Freezer 220-240 Volt 50/60 HZ", retrieved online on Dec. 29, 2025, at: https://www.samstores.com/product-frigidaire-mfc09v4gw-chest-freezer-220-240-volt-5060-hz-7985.html?srsltid=aFmBOoq-kqrX3TYBATp2MXlyQoNj5_mgWVenhVW7UNyzTO8jilcorAAG, in 3 pages (2015).

Van Leeuwen et al., "Sequential hypothermic and normothermic machine perfusion enables safe transplantation of high-risk donor livers", American Journal of Transplantation, vol. 22(6):1658-1670 (2022).

* cited by examiner

METHOD FOR HYPOTHERMIC TRANSPORT OF BIOLOGICAL SAMPLES

INCORPORATION BY REFERENCE TO ANY PRIORITY APPLICATIONS

This application is a continuation of U.S. patent application Ser. No. 19/041,796, filed Jan. 30, 2025, which claims the benefit of priority under 35 U.S.C. § 119(e) to U.S. Provisional Patent Application No. 63/549,145, filed Feb. 2, 2024, and U.S. Provisional Patent Application No. 63/727,110, filed Dec. 2, 2024. All of these applications are hereby incorporated by reference herein in their entireties. Any and all applications for which a foreign or domestic priority claim is identified in the Application Data Sheet as filed with the present application are hereby incorporated by reference under 37 CFR 1.57.

FIELD

This disclosure relates to systems and method for hypothermic transport of biological samples, for example tissues for donation. The systems and methods provide a secure, sterile, and temperature-controlled environment for transporting the samples.

BACKGROUND

There is a critical shortage of donor organs. Hundreds of lives could be saved each day if more organs (heart, kidney, lung, etc.) were available for transplant. While the shortage is partly due to a lack of donors, there is a need for better methods of preserving and transporting donated organs. Current storage and preservation methods allow only a small time window between harvest and transplant, typically on the order of hours. These time windows dictate who is eligible to donate organs and who is eligible to receive the donated organs. These time windows also result in eligible organs going unused because they cannot be transported to a recipient in time.

Current organ perfusion devices often require a variable pump to adjust flow rate during transport. This can lead to imprecision due to lag time and/or human error. Certain current organ perfusion devices draw fluid from an external source rather than using a closed loop system, which can result in complications due to additional variables.

Current organ perfusion devices typically utilize an expensive, re-usable capital component (pump) and single-use components (cassette), and require user input and monitoring for temperature, perfusion pressure, and renal flow. The need for active monitoring by a health care provider who must listen for alarms and intervene (e.g., add ice to ensure adequate kidney cooling) and adjust settings during transport create staffing challenges and limits the options for transporting organs to the transplant recipients. Specifically, it has become common for kidneys, unlike other organs, to be transported by air unaccompanied. In such, it is impractical to transport kidneys in current perfusion devices unaccompanied.

Improved transport and storage for organs would increase the pool of available organs while improving outcomes for recipients.

SUMMARY

The disclosure provides an improved system for transporting biological samples, e.g., tissues, such as donor organs. In certain examples, this improved system may greatly expand the window of time for organ transportation and, consequently, make many more organs available for donation. Additionally, the samples may be healthier upon arrival, as compared to state-of-the-art transport methods. In some embodiments, organ perfusion can prolong viability of donor organs, for example kidneys, by ensuring uniform cooling and flushing out of metabolites. Current organ perfusion devices often require monitoring during transportation to ensure that the fluid flow is within a desired range. Such an approach can require a user to increase or decrease a pump speed, either manually or by an automatic controller. In systems that use an automatic controller, the pump parameters can be determined by an algorithm based on pressure sensor measurements. Such as approach may lead to imprecision based on inaccuracy of the sensors and the algorithm. Further, the feedback loop can also cause delay in adjusting the pump parameters.

Embodiments of the disclosed system for organ transport overcome the shortcomings of the prior art by delivering a flow of preservation fluid at pressures acceptable to the organ anatomy without requiring manual operation or a control algorithm. For example, the flow regulator valve can ensure that flow through the organ is acceptable, varying the amount of fluid pumped into the vessel based on the vessel's resistance. The flow regulator valve can provide a mechanical check that is precise and instantaneous. A pressure dampener can be used to provide constant flow, reducing pulsation caused by the peristaltic pump. The flow regulator valve in combination with the pressure dampener can be especially advantageous as it ensures constant flow through the organ perfusion system.

In some embodiments, the systems described herein relate to hypothermic transport of an organ, for example a kidney, a lung, a heart, or a liver, including: a transport container configured to receive an organ, the transport container configured to be at least partially filled with preservation fluid, the transport container including: a fluid circuit including: an inlet configured to be in communication with the preservation fluid in the transport container; a flow regulator valve in fluid communication with the inlet, the flow regulator valve configured to release the preservation fluid from the fluid circuit into the transport container at a rate based on renal resistance of the organ; and an outlet in fluid communication with the flow regulator valve and the organ; and a pump configured to pump the preservation fluid from the inlet to the organ, the pump configured to operate independently of renal resistance.

In some embodiments, the transport container further includes an organ rest configured to support the organ. In some embodiments, the systems described herein include an organ adapter configured to seal a vessel of the organ, the organ adapter adjustable along a groove of the organ rest. In some embodiments, the systems described herein include a pressure dampener, wherein the pressure dampener is configured to reduce pulsation in the fluid circuit caused by the pump. In some embodiments, the pump is a peristaltic pump. In some embodiments, the pump is a centrifugal pump, a diaphragm pump, a piston pump, or a gear pump. In some embodiments, the flow regulator valve releases the preservation fluid from the fluid circuit into the transport container at a higher rate when renal resistance is higher. In some embodiments, the transport container further includes: a plurality of posts; and an organ retainer adjustably couplable to the plurality of posts. In some embodiments, the transport container further includes a one-way valve in fluid communication with the fluid circuit, the one-way valve configured to take in preservation fluid from the transport container when fluid is drawn out of the fluid circuit. In some embodiments, the transport container further includes a temperature sensor. In some embodiments, the systems described herein include a lid including a fill port and a vent port. In some embodiments, the systems described herein include an accumulation chamber configured to seal to at least one of the fill port and the vent port, the accumulation chamber including a balloon configured to expand when the preservation fluid expands and contract when the preservation fluid contracts. In some embodiments, the organ adapter includes: a cannula including a barb, the cannula configured to seal to the vessel of the organ; and a cannula receiver configured to couple with the barb.

In some embodiments, the methods described herein relate to hypothermic transport of an organ, for example a kidney, a lung, a heart, or a liver, the method including: placing an organ in a transport container, the transport container including an organ adapter; sealing the organ adapter to a vessel of the organ; placing a lid on the transport container; filling the transport container at least partially with preservation fluid through a fill port in the lid; and activating a pump, the pump configured to pump the preservation fluid from the transport container to a flow regulator valve and the organ adapter, the flow regulator valve configured to release the preservation fluid into the transport container at a rate based on renal resistance of the organ, and the pump configured to operate independently of renal resistance.

In some embodiments, the methods described herein include placing the organ on an organ rest. In some embodiments, the methods described herein include adjusting the organ adapter along a groove of the organ rest. In some embodiments, the methods described herein include attaching an organ retainer to a plurality posts in the transport container such that the organ retainer secures the organ. In some embodiments, the methods described herein include sealing an accumulation chamber to at least one of the fill port or a vent port on the lid.

In some embodiments, the systems described herein relate to hypothermic transport of an organ, for example a kidney, a lung, a heart, or a liver, including: a transport container configured to receive an organ, the transport container configured to be at least partially filled with preservation fluid; a pump configured to pump the preservation fluid from the transport container to the organ in a fluid circuit, the pump configured to operate independently of renal resistance; and a flow regulator valve in fluid communication with the fluid circuit, the flow regulator valve configured to release the preservation fluid from the fluid circuit into the transport container at a rate based on renal resistance of the organ.

In some embodiments, the transport container further includes an organ rest configured to support the organ. In some embodiments, the systems described herein include an organ adapter configured to seal a vessel of the organ, the organ adapter adjustable along a groove of the organ rest. In some embodiments, the systems described herein include a pressure dampener, wherein the pressure dampener is configured to reduce pulsation caused by the pump. In some embodiments, the pump is a peristaltic pump. In some embodiments, the pump is a centrifugal pump, a diaphragm pump, a piston pump, or a gear pump. In some embodiments, the flow regulator valve releases the preservation fluid from the fluid circuit into the transport container at a higher rate when renal resistance is higher. In some embodiments, the transport container further includes: a plurality of posts; and an organ retainer adjustably couplable to the plurality of posts. In some embodiments, the transport container further includes a one-way valve in fluid communication with the fluid circuit, the one-way valve configured to take in preservation fluid from the transport container when fluid is drawn out of the fluid circuit. In some embodiments, the transport container further includes a temperature sensor. In some embodiments, the systems described herein include a lid including a fill port and a vent port. In some embodiments, the systems described herein include an accumulation chamber configured to seal to at least one of the fill port and the vent port, the accumulation chamber including a balloon configured to expand when the preservation fluid expands and contract when the preservation fluid contracts. In some embodiments, the organ adapter includes: a cannula including a barb, the cannula configured to seal to the vessel of the organ; and a cannula receiver configured to couple with the barb.

In some embodiments, the systems described herein relate to hypothermic transport of an organ, for example a kidney, a lung, a heart, or a liver, including: a canister configured to contain an organ and preservation fluid; an inner lid configured to couple with the canister; an outer canister configured to couple with the inner lid, the outer canister including a tube; and a pump configured to pump the preservation fluid in the tube such that the preservation fluid flows from the canister to the inner lid, from the inner lid to the outer canister, from the outer canister to the tube, from the tube to the outer canister, from the outer canister to the inner lid, from the inner lid to the organ, and from the organ to the canister.

In some embodiments, the systems described herein relate to hypothermic transport of an organ, for example a kidney, a lung, a heart, or a liver, including: a canister configured to receive an organ, the canister containing preservation fluid; a port between the canister and an environment; and an accumulation chamber configured to seal to the port, the accumulation chamber including a balloon configured to expand when the preservation fluid expands and contract when the preservation fluid contracts.

In some embodiments, the methods described herein relate to hypothermic transport of an organ, for example a kidney, a lung, a heart, or a liver, the method including: placing an organ in a canister; filling the canister with preservation fluid through a fill port; venting the canister of fluid through a vent port; and attaching an accumulation chamber on at least one of the fill port or the vent port, the accumulation chamber including a balloon configured to expand when the preservation fluid expands and contract when the preservation fluid contracts.

In some embodiments, the systems described herein relate to hypothermic transport of an organ, for example a kidney, a lung, a heart, or a liver, including: a canister configured to receive an organ, the canister including: an organ rest configured to support the organ; and a plurality of posts; and an organ retainer adjustably couplable to the plurality of posts.

In some embodiments, the methods described herein relate to hypothermic transport of an organ, for example a kidney, a lung, a heart, or a liver, the method including: placing an organ in a canister, the canister including an organ rest configured to support the organ and a plurality of posts; and coupling an organ retainer to the plurality of posts at a position such that the organ retainer contacts the organ.

In some embodiments, the systems described herein relate to hypothermic transport of an organ, for example a kidney, a lung, a heart, or a liver, including: a canister configured to receive an organ; an organ rest inside the canister configured to support the organ, the organ rest including a groove; and an organ adapter configured to seal to a vessel of the organ, the organ adapter movable along the groove.

In some embodiments, the organ adapter includes: a cannula configured to seal to the vessel of the organ; and a cannula receiver on the organ rest configured to couple with the cannula.

In some embodiments, the methods described herein relate to hypothermic transport of an organ, for example a kidney, a lung, a heart, or a liver, the method including: placing an organ in a canister on an organ rest, the organ rest including a groove; sealing an organ adapter to a vessel of the organ; moving the organ adapter along the groove; and locking the organ adapter in place such that a renal artery of the organ is under tension.

In some embodiments, sealing the organ adapter to the vessel of the organ includes: sealing the vessel of the organ with a cannula; and coupling the cannula to a cannula receiver on the organ rest.

In some embodiments, the techniques described herein relate to an apparatus substantially as shown and/or described. In some embodiments, the techniques described herein relate to a method substantially as shown and/or described. In some embodiments, the techniques described herein relate to a system substantially as shown and/or described.

In some examples, the systems for hypothermic transport of a biological sample described herein can include: a transport container configured to receive an organ, the transport container configured to be at least partially filled with preservation fluid, the transport container including: a fluid circuit including: an inlet configured to be in communication with the preservation fluid in the transport container; a flow regulator valve in fluid communication with the inlet, the flow regulator valve configured to regulate a flow rate from the fluid circuit to the organ based on at least one organ parameter; and an outlet in fluid communication with the flow regulator valve and the organ; and a pump configured to pump the preservation fluid from the inlet to the organ, the pump configured to operate independently of the at least one organ parameter.

In some examples, the at least one organ parameter includes at least one of vessel resistance, organ temperature, or flow rate through the organ. In some examples, the transport container further includes an organ rest configured to support the organ. In some examples, the system can include an organ adapter configured to seal a vessel of the organ, the organ adapter adjustable along a groove of the organ rest. In some examples, the system can include a pressure dampener, wherein the pressure dampener is configured to reduce pulsation in the fluid circuit caused by the pump. In some examples, the pump is a peristaltic pump. In some examples, the transport container further includes: a plurality of posts; and an organ retainer adjustably couplable to the plurality of posts. In some examples, the transport container further includes a one-way valve in fluid communication with the fluid circuit, the one-way valve configured to take in preservation fluid from the transport container when fluid is drawn out of the fluid circuit. In some examples, the system can include an accumulation chamber configured to seal to a port on a lid of the transport container, the accumulation chamber including a balloon configured to expand when the preservation fluid expands and contract when the preservation fluid contracts. In some examples, the system can include a bubble trap integrated in the fluid circuit.

In some examples, the systems for hypothermic transport of a biological sample described herein can include: a transport container configured to receive an organ, the transport container configured to be at least partially filled with preservation fluid; a pump configured to pump the preservation fluid from the transport container to the organ in a fluid circuit, the pump configured to operate independently of vessel resistance; and a flow regulator valve in fluid communication with the fluid circuit, the flow regulator valve configured to regulate a flow rate from the fluid circuit to the organ based on at least one organ parameter.

In some examples, the at least one organ parameter includes at least one of vessel resistance, organ temperature, or flow rate through the organ. In some examples, the transport container further includes an organ rest configured to support the organ. In some examples, the system can include an organ adapter configured to seal a vessel of the organ, the organ adapter adjustable along a groove of the organ rest. In some examples, the system can include a pressure dampener, wherein the pressure dampener is configured to reduce pulsation caused by the pump. In some examples, the pump is a peristaltic pump. In some examples, the transport container further includes: a plurality of posts; and an organ retainer adjustably couplable to the plurality of posts. In some examples, the transport container further includes a one-way valve in fluid communication with the fluid circuit, the one-way valve configured to take in preservation fluid from the transport container when fluid is drawn out of the fluid circuit. In some examples, the system can include a lid including a fill port and a vent port. In some examples, the system can include an accumulation chamber configured to seal to at least one of the fill port and the vent port, the accumulation chamber including a balloon configured to expand when the preservation fluid expands and contract when the preservation fluid contracts.

In some examples, the methods for hypothermic transport of a biological sample described herein can include: sealing a biological sample adapter to a vessel of a biological sample; placing the biological sample in a transport container; sealing a lid on the transport container; filling the transport container at least partially with preservation fluid through a fill port in the lid; and activating a pump, the pump configured to pump the preservation fluid from the transport container to a flow regulator valve and the biological sample adapter, the flow regulator valve configured to regulate a flow rate into the biological sample based on at least one biological sample parameter, and the pump configured to operate independently of the at least one biological sample parameter.

In some examples, the at least one biological sample parameter includes at least one of vessel resistance, biological sample temperature, or flow rate through the biological sample. In some examples, the method can include placing the biological sample on a biological sample rest. In some examples, the method can include coupling the biological sample adapter to a cannula receiver on the biological sample rest. In some examples, the method can include adjusting the biological sample adapter along a groove of the biological sample rest. In some examples, the method can include locking the biological sample adapter in place along the groove such that the vessel of the biological sample is under tension. In some examples, the method can include attaching a biological sample retainer to a plurality posts in the transport container such that the biological sample retainer secures the biological sample. In some examples, the method can include venting the transport container of fluid through a vent port. In some examples, the method can include attaching an accumulation chamber on at least one of the fill port or the vent port, the accumulation chamber including a balloon configured to expand when the preservation fluid expands and contract when the preservation fluid contracts. In some examples, the method can include preserving the biological sample for greater than 5 hours without adjusting parameters of the pump.

In some examples, the methods for hypothermic transport of a biological sample described herein can include: pumping, using a pump, preservation fluid from a transport container to an inlet of a fluid circuit at a rate independent of vessel resistance of a biological sample; pumping, using the pump, the preservation fluid from the inlet to a flow regulator valve; regulating, using the flow regulator valve, a flow rate into the biological sample based on at least one biological sample parameter; and pumping, using the pump, the preservation fluid from the flow regulator valve to a biological sample adapter in fluid communication with the biological sample.

In some examples, the at least one biological sample parameter includes at least one of vessel resistance, biological sample temperature, or flow rate through the biological sample. In some examples, the method can include applying tension to a vessel of the biological sample with the biological sample adapter while the biological sample is on a biological sample rest. In some examples, the method can include expanding a balloon in an accumulation chamber when the preservation fluid expands, wherein the accumulation chamber is attached to a port of a lid of the transport container. In some examples, the method can include cooling the biological sample with phase change material on an outer lid sealed to the transport container. In some examples, the method can include reducing pulsation in the fluid circuit with a pressure dampener. In some examples, the method can include measuring a pressure in the fluid circuit. In some examples, the method can include displaying the pressure in the fluid circuit on a display of the transport container. In some examples, the method can include measuring a temperature in the fluid circuit. In some examples, the method can include displaying the temperature in the fluid circuit on a display of the transport container.

DETAILED DESCRIPTION

Figure 1A:
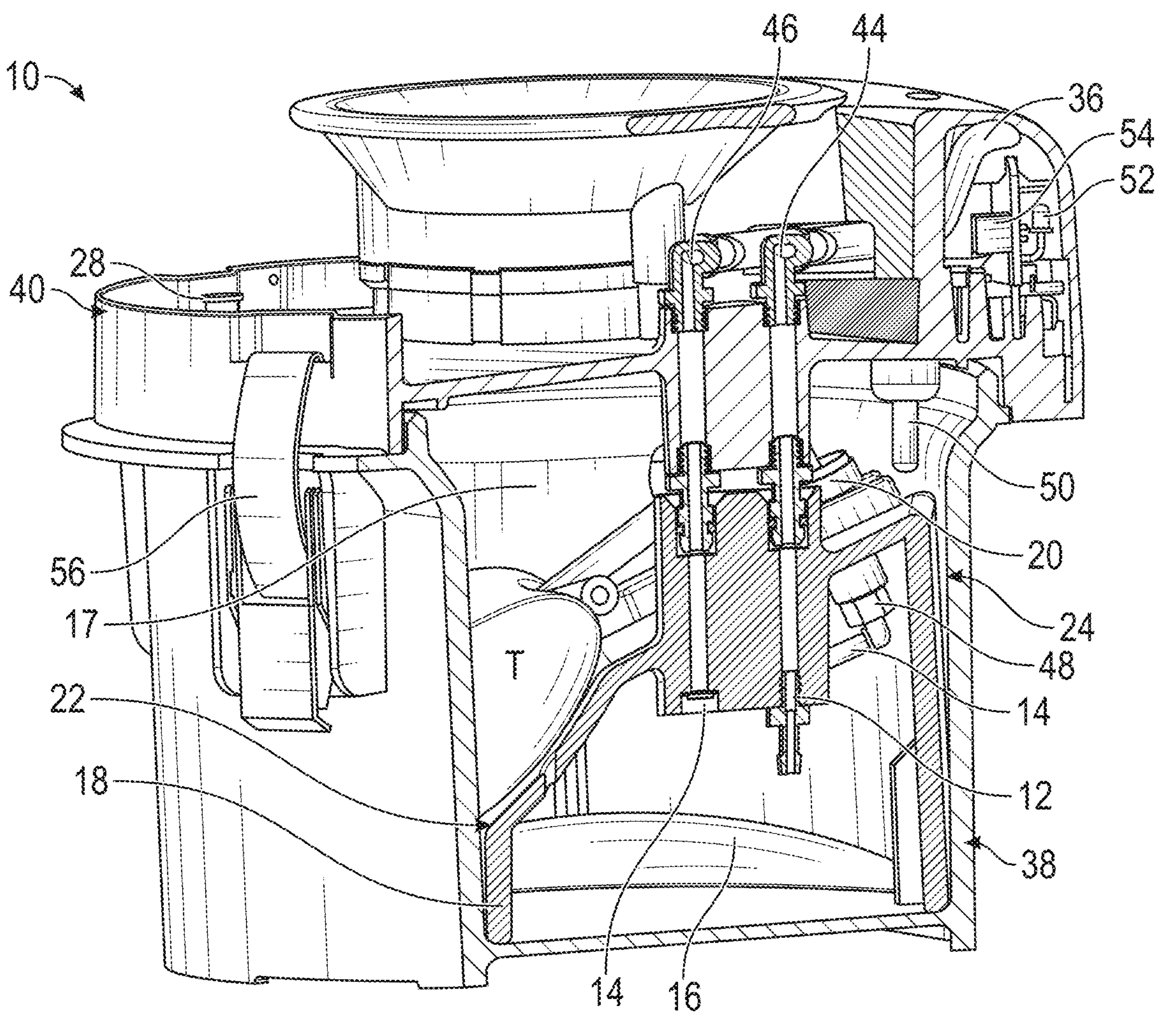
FIG. 1A is a side, cross-sectional view of an example of an organ preservation apparatus.

The disclosed systems for hypothermic transport of samples provide a sterile, temperature-stabilized environment for transporting samples while providing an ability to perfuse organs with a constant pump system. Because of these improvements, users of examples of the systems described herein can reliably transport samples over much greater distances, thereby substantially increasing the pool of available tissue donations. Additionally, because the tissues may be in better condition upon delivery, the long-term prognosis for the recipient may be improved.

In examples, the systems described herein may use a pump to perfuse one or more organs with fluid from within the canister in a cycle. The pump can operate at a constant rate so that preservation fluid is consistently being circulated throughout the system in a closed loop. A fluid channel may carry the fluid from the chamber to the pump and then to the organ. The organ can release the fluid back into the chamber. A flow regulator valve or manifold in line with the fluid channel can allow some fluid to be released into the chamber before it reaches the organ when the resistance of the cannulated organ is above a threshold. For instance, the resistance of the renal artery of the kidney can determine how much fluid is released from the manifold as opposed to how much enters the kidney.

The pump can be a peristaltic pump in contact with the fluid channel or any other suitable pump. The point of contact with the pump can be outside the canister containing the organ. Once the pump is turned on, the system can operate without any inputs or outputs during transport. The same fluid can be circulated throughout transportation or storage. The system can include a pressure dampener that reduces pulsation of the flow caused by the pump.

Hypothermic transport systems such as those described herein can comprise a self-purging preservation apparatus and an insulated transport container. The self-purging preservation apparatus may receive the tissue for transport, and keep it suspended or otherwise supported in a surrounding pool of preservation solution. In some examples, the preservation solution can be chilled to around 4° C. The preservation solution may be chilled to below 4° C. The self-purging preservation apparatus may comprise a number of configurations suitable to transport tissues hypothermically.

In some embodiments, a transport device may be configured to self-purge excess fluid (e.g., liquid and/or gas). For example, in some embodiments, such a device includes a lid assembly in which at least a portion of the lid assembly is inclined with respect to a horizontal axis. The inclined portion of the lid assembly may be configured to facilitate the flow of fluid towards a vent port disposed at substantially the highest portion of a chamber of the lid assembly. In this manner, excess fluid can escape the device via the purge port. Also in this manner, when excess liquid is expelled from the device via the purge port, an operator of the device can determine that any excess gas has also been purged from the device, or at least from within a tissue chamber of the device, because the gas is lighter than the liquid and will move towards and be expelled via the purge port before excess liquid.

As used in this specification, the singular forms "a," "an" and "the" include plural referents unless the context clearly dictates otherwise. Thus, for example, the term "a fluid" is intended to mean a single fluid or a combination of fluids.

As used herein, "a fluid" refers to a gas, a liquid, or a combination thereof, unless the context clearly dictates otherwise. For example, a fluid can include oxygen, carbon dioxide, or another gas. In another example, a fluid can include a liquid. Specifically, the fluid can be a liquid perfusate. In still another example, the fluid can include a liquid perfusate with a gas, such as oxygen, mixed therein or otherwise diffused therethrough.

As used herein, "tissue" refers to any tissue of a body of a patient, including tissue that is suitable for being replanted or suspected of being suitable for replantation. Tissue can include, for example, muscle tissue, such as, for example, skeletal muscle, smooth muscle, or cardiac muscle. Specifically, tissue can include a group of tissues forming an organ, such as, for example, the skin, lungs, cochlea, heart, bladder, liver, kidney, or other organ. In another example, tissue can include nervous tissue, such as a nerve, the spinal cord, or another component of the peripheral or central nervous system. In still another example, tissue can include a group of tissues forming a bodily appendage, such as an arm, a leg, a hand, a finger, a thumb, a foot, a toe, an car, genitalia, or another bodily appendage. While the systems are described as relating to the transport of tissues, such as organs, it is also envisioned that the systems could be used for the transport of body fluids, which may be held in another container within the self-purging preservation apparatus. Body fluids may include blood and blood products (whole blood, platelets, red blood cells, etc.) as well as other body fluids for preservation.

Figure 1B:
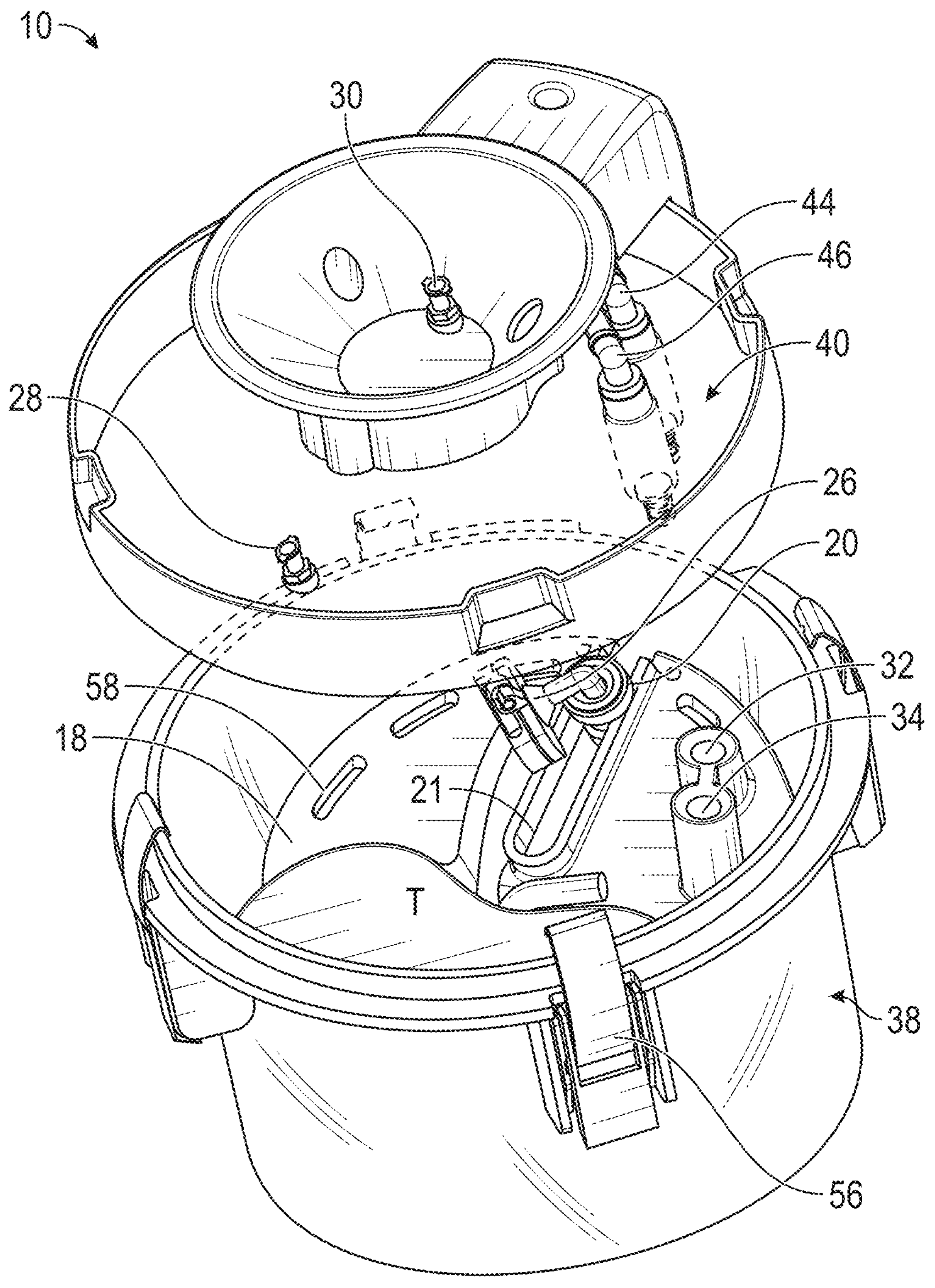
FIG. 1B is a top, angled view of the example of the organ preservation apparatus of FIG. 1A with the inner lid uncoupled from the canister.
Figure 1C:
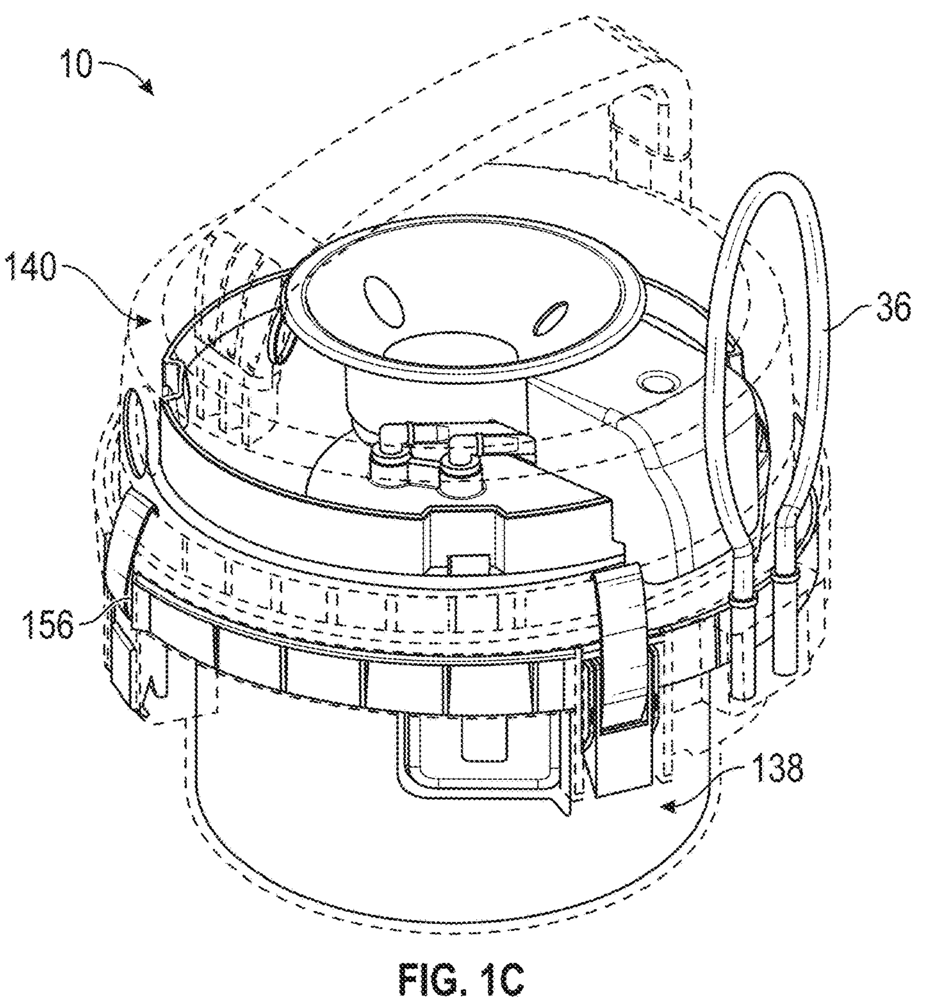
FIG. 1C is a top, angled view of the example of the organ preservation apparatus of FIG. 1A with the inner lid and outer lid coupled to the canister.

FIG. 1A is a cross-sectional, side view of an example of an organ preservation apparatus. FIG. 1B is a top, angled view of the example of the organ preservation apparatus of FIG. 1A with the inner lid 40 uncoupled from the canister 38. FIG. 1C is a top, angled view of the example of the organ preservation apparatus of FIG. 1A with the inner lid 40 and outer lid 42 coupled to the canister 38.

The apparatus 10 can be configured to store a biological sample T. The apparatus 10 can be configured to perfuse the biological sample T using a constant pump system, as described with respect to FIGS. 2A and 2B. Pumping preservation fluid in the biological sample T can extend the preservation of the sample. The biological sample T can be an organ, for example a kidney. In other embodiments, the organ can be a lung, a heart, or a liver. The constant pump system can be advantageous to allow flow through the biological sample T without requiring changes to the pump rate. The constant pump system, once activated, can operate without intervention throughout transportation.

The apparatus 10 can include an inner lid 40 and a canister 38 that can be coupled using clamps 56. An outer lid 140 and outer canister 138 can contain the canister 38 and inner lid 40 as described with respect to FIG. 3A. The outer lid 140 and outer canister 138 can be coupled using clamps 156.

Figure 7A:
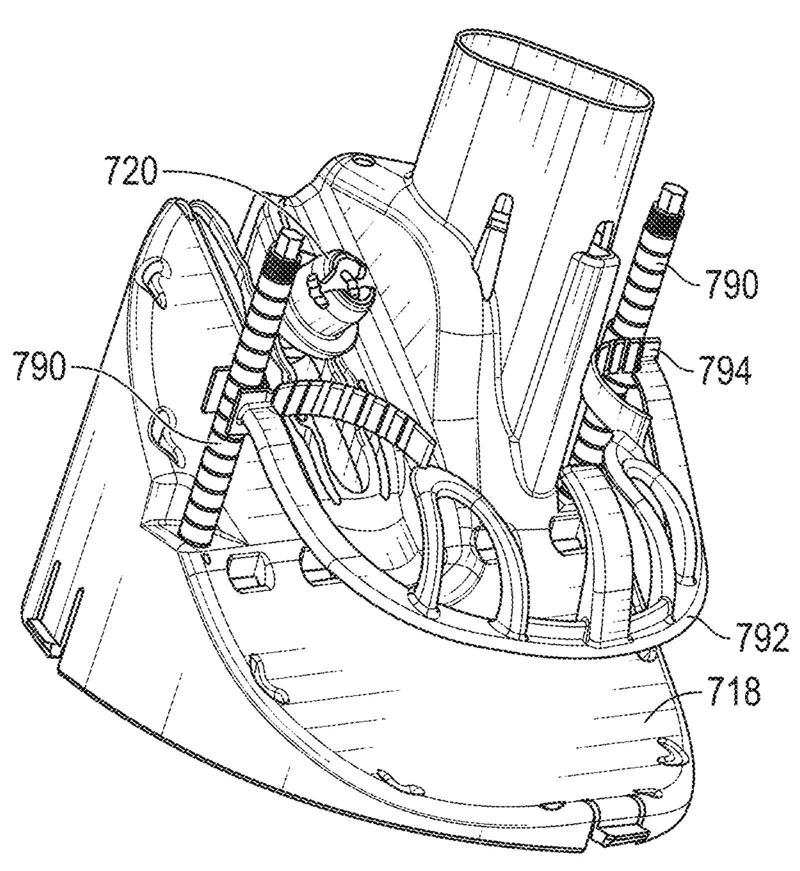
FIG. 7A illustrates an example of a kidney rest with posts and an organ retainer.
Figure 7B:
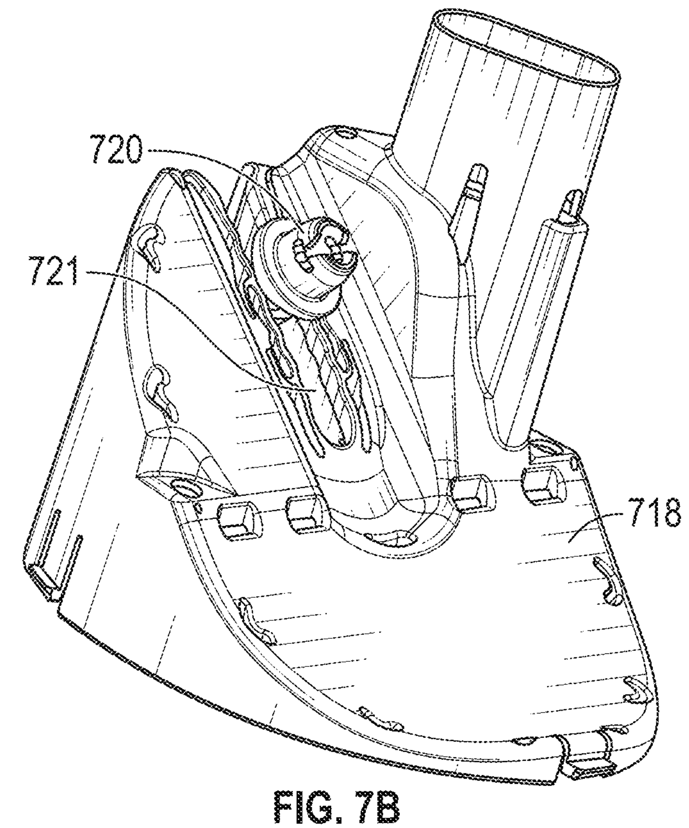
FIGS. 7B-7C illustrate an example of the kidney rest of FIG. 7A.
Figure 7C:
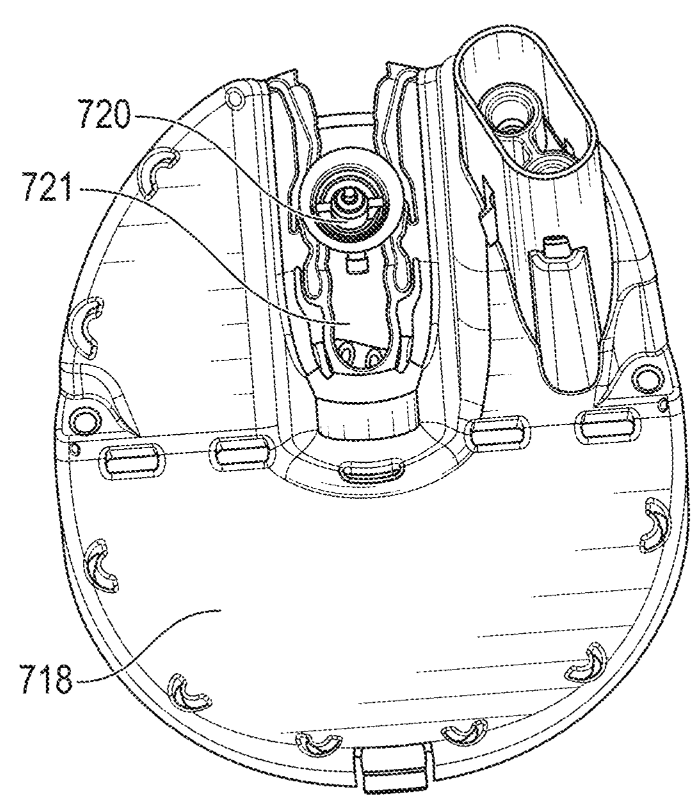

The biological sample T can be positioned on an organ rest 18, for example an organ rest as described with respect to FIGS. 7B and 7C. The biological sample T can be connected to a cannula 26, as described with respect to FIGS. 8A, 8B, 9A, and 9B. The cannula 26 can be connected to a cannula receiver 20. The cannula receiver 20 can be positioned in a groove 21 of the organ rest. The pumping chamber 16 beneath the organ rest 18 can be filled with fluid, for example preservation fluid. The preservation fluid can be pumped from the pumping chamber 16 to an inlet 12. The entire canister 38 can be substantially filled with preservation fluid. The inlet 12 can include a filter as described with respect to FIG. 2B.

In certain examples, the inner lid 40 can include a fill port 28 and a vent port 30. The canister 38 can be filled with preservation through into the fill port 28, for example until the canister 38 is substantially filled. Gas and fluid can exit the canister from the vent port 30 while the canister 38 is being filled. The fill port 28 can be configured to permit fluid (e.g., perfusate) to be introduced to the canister 38. In this manner, fluid can be introduced into the canister 38 as desired by an operator of the apparatus. For example, in some embodiments, a desired amount of perfusate is introduced into the canister 38 via the fill port 28, such as before disposing the tissue T in the canister 38 and/or while the biological sample T is received in the tissue chamber. In some embodiments, the fill port 28 is a unidirectional port, and thus is configured to prevent the flow of fluid from the canister 38 to an area external to the tissue chamber through the port. In some embodiments, the fill port 28 includes a luer lock. The canister 38 may be of any suitable volume necessary for receiving the tissue T and a requisite amount of fluid for maintaining viability of the tissue T. In one embodiment, for example, the volume of the canister 38 is approximately 2 liters. Once the canister 38 is substantially filled with preservation fluid, the fill port 28 and vent port 30 can be sealed. After filling, an accumulation chamber can be positioned on the fill port 28, as described with respect to FIGS. 6A and 6B.

Fluid, for example gas, in the canister 38 can be vented through the vent port 30 and/or the fill port 28. The vent port 30 can be configured to permit fluid to flow into the atmosphere external to the apparatus 10. In some embodiments, the vent port 30 is configured for unidirectional flow, and thus is configured to prevent a fluid from being introduced into the canister 38 via the port (e.g., from a source external to the apparatus 10). In some embodiments, the vent port 30 includes a luer lock. After venting, an accumulation chamber can be positioned on the vent port 30, as described with respect to FIGS. 6A and 6B. The accumulation chamber can minimize impacts of external forces or pressures impacting the pressure of the fluid.

In some examples, when the inner lid 40 is coupled with the canister 38, the inlet 12 can be in fluid communication with the lid inlet 44. The lid inlet 44 can be in fluid communication with an outer tube 36. The outer tube 36 can be in contact with a pump. The outer tube 36 can be in fluid communication with a lid outlet 46. When the inner lid 40 is coupled with the canister 38, the lid outlet 46 can be in communication with the outlet 14. The outlet 14 can include a flow regulator valve 48, or a pressure relief valve. The outlet can be in fluid communication with the cannula receiver 20. A pressure sensor 52 and pressure damper 54 can be positioned near the outer tube 36 in the inner lid 40. A temperature sensor 50 can be positioned near on the bottom of the inner lid 40 near the cannula receiver 20 when the inner lid 40 and the canister 38 are coupled. The temperature sensor 50 can measure the temperature of the preservation fluid in the canister 38. Fluid can flow from the outlet 14 to the biological sample T, for example through the cannula receiver 20 and the cannula 26. Fluid can flow into the biological sample T through a vessel such as a renal artery of a kidney. Fluid can flow out of the biological sample through a vessel such as a renal vein or ureter of a kidney. After exiting the biological sample T, the fluid can collect in the organ chamber 17.

As shown in FIG. 1A, the organ rest 18 can be inclined at an angle. The organ rest 18 can incline from a lower point on one side 22 to a higher point on the other side 24. The incline of the organ rest 18 can be advantageous to maintain tension on a cannulated vessel of the biological sample T. The cannulated vessel can be an artery, for example a renal artery. In some embodiments, the cannulated vessel can be a renal vein or ureter. The organ rest 18 can support the biological sample. The organ rest 18 can be curved to accommodate a bottom surface of the biological sample T.

In some examples, the organ chamber 17 can be formed by the canister 38 and the organ rest 18 above the pumping chamber 16. The organ rest 18 can be non-permeable and can have apertures 58 to allow fluid to move between the organ chamber 17 and the pumping chamber 16.

In some examples, the organ rest 18 can be integral with the bottom of the canister 38 or removably connected to the canister 38. The organ rest 18 can have a groove 21. The groove 21 can be a narrow opening with a raised portion surrounding it. The cannula receiver 20 can be slidably positioned in the groove 21, such that the device is adjustable. The cannula receiver 20 can be locked into a position along the groove 21 based on the length of the cannulated vessel, for example the length of the renal artery. The cannula receiver 20 can be positioned such that there is tension on the cannulated vessel when the biological sample T is secured on the organ rest 18. A user can connect the cannula 26 to the biological sample T, connect the cannula 26 to the cannula receiver 20, move the cannula receiver 20 along the groove 21 to adjust for vessel length, and lock the cannula receiver 20 in place. The cannula receiver 20 and/or the cannula 26 can be referred to as an organ adapter, for example a kidney adapter.

In some examples, the organ rest 18 can have a retention mechanism to secure the biological sample T in place. This can prevent lateral and vertical movement of the biological sample T during transportation. The retention mechanism can be any suitable device such as, for example, a net, a cage, a sling, a strap, or the like. The retention mechanism can be attached to posts on the organ rest, as described with respect to FIG. 7A. In some embodiments, the apparatus 10 includes a basket (not shown) or other support mechanism configured to support the tissue T when the tissue T is on the organ rest 18 or otherwise received in the apparatus 10.

In certain examples, the sterile canister can be constructed from a sterilizable material, i.e., made of a material that can be sterilized by steam (autoclave), chemically, or via UV irradiation, or another suitable form of sterilization. Sterilization can prevent tissues from becoming infected with viruses, bacteria, etc., during transport. In a typical embodiment, the sterile canister can be delivered in a sterile condition and sealed in sterile packaging. In some embodiments, the sterile canister apparatus will be re-sterilized prior to reuse, for example at a hospital. In other embodiments, the sterile canister will be disposable.

In examples, the systems, methods, and apparatuses described herein for hypothermic transport of tissues described herein may provide for the transport of biological samples (e.g., tissue, organs, or body fluids) over long distances and time periods while maintaining a temperature of 4-8° C., or in another example, 2-10° C. For example, temperature may be controlled for at least about 6 h, 12 h, 24 h, 48 h, or more time. Systems of the disclosure can enable medical professionals to keep tissues (e.g., organs) in a favorable hypothermic environment for extended periods of time, thereby allowing more time between harvest and transplant.

In some examples, in use, the biological sample T is coupled to the cannula 26 and secured on the organ rest 18. A desired amount of perfusate is introduced into the canister 38 via the fill port 28. The canister 38 can be filled with the perfusate such that the perfusate volume rises to the highest portion of the tissue chamber. The canister 38 can be filled with an additional amount of perfusate such that the perfusate flows from the organ chamber 17 through the apertures 58 into the pumping chamber 16. The canister 38 can continue to be filled with additional perfusate until all atmospheric gas that initially filled the canister 38 rises and escapes through the vent port 30. Because the gas will be expelled via the vent port 30 before any excess perfusate is expelled (due to gas being lighter, and thus more easily expelled, than liquid), an operator of the apparatus 10 can determine that substantially all excess gas has been expelled from the pumping chamber when excess perfusate is released via the port. Due to the release of the excess gas, in certain examples, the apparatus 10 can be characterized as self-purging. When perfusate begins to flow out of the vent port 30, the apparatus 10 is in a "purged" state (i.e., all atmospheric gas initially within the canister 38 has been replaced by perfusate). When the purged state is reached, the operator can close both the fill port 28 and vent port 30, preparing the apparatus 10 for operation.

The canister 38 can be constructed of any suitable material. In some embodiments, the canister 38 is constructed of a material that permits an operator of the apparatus 10 to view at least one of the tissue T or the perfusate received in the organ chamber 17. For example, in some embodiments, the canister 38 is substantially transparent. In another example, in some embodiments, the canister 38 is substantially translucent. Lastly, in certain examples, the canister may be opaque to obscure viewing of the tissue. The organ chamber 17 can be of any suitable shape and/or size. For example, in some embodiments, the organ chamber 17 can have a perimeter that is substantially oblong, oval, round, square, rectangular, cylindrical, or another suitable shape. The canister 38 and organ rest 18 can be plastic. The apparatus 10 can be easily transportable.

In some examples, the flow regulator valve 48 can release fluid from the fluid channel rather than allowing it to flow to the biological sample T when the resistance of the cannulated vessel is above a threshold. Once fluid enters the flow regulator valve 48, it can flow either directly to the biological sample or back into the organ chamber 17. The flow regulator valve 48 can be a mechanical device that releases fluid when a certain pressure is exceeded. The flow regulator valve 48 can close more when pressure decreases such that increased flow is directed to the biological sample T. The flow regulator valve 48 can be variable such that when pressure or renal resistance decreases, more flow is directed to the kidney. Resistance in the cannulated vessel can be higher, for example, when the organ is exposed to low temperatures before transport. A higher resistance of the vessel of the kidney can result in higher pressure. Setting the relief valve 48 to allow an optimal or enhanced flow of fluid into the cannulated vessel can obviate the need to change pump parameters during transportation. The flow regulator valve 48 can be metal, for example stainless steel. In some embodiments, the flow regulator valve 48 may be pre-set at a pressure threshold or series of pressure thresholds. In another embodiment, the flow regulator valve 48 may be adjustable, allowing for a user to set pressure thresholds.

In some examples, when pressure is below the threshold, the fluid can be allowed to flow into the biological sample T. For high renal resistance, the pressure threshold can be 65 mmHg. In some embodiments, for high renal resistance, the pressure threshold can be 60-70 mmHg. In some embodiments, for high renal resistance, the pressure threshold can be 50-80 mmHg. For medium renal resistance, the pressure threshold can be approximately 30-65 mmHg. In some embodiments, for medium renal resistance, the pressure threshold can be approximately 10-100 mmHg. For low renal resistance, the pressure threshold can be approximately 30 mmHg. In some embodiments, for low renal resistance, the pressure threshold can be approximately 10-50 mmHg. In some examples, the device can maintain a pressure operating range of 0 mmHg to 50 mmHg with a flow operating range of 0 mL/min to 150 mL/min.

In certain examples, high renal vascular resistance can mean a perfusion pressure of greater than approximately 35 mmHg. In some examples, medium renal vascular resistance can mean a perfusion pressure of between approximately 25 and approximately 35 mmHg. In some examples, low renal vascular resistance can mean a perfusion pressure of less than approximately 25 mmHg.

The flow regulator valve 48 can operate such that flow rate to the kidney varies based on pressure and/or renal resistance. Renal resistance can be measured in units of mmHg*min/mL. In some embodiments, when pressure is greater than 42 mmHg and/or renal resistance is greater than 1.55, the flow rate to the kidney can be less than or equal to 30 mL/min. In some embodiments, when pressure is greater than 30-50 mmHg and/or renal resistance is greater than 0.5-2.5, the flow rate to the kidney can be less than or equal to 10-50 mL/min. In some embodiments, when pressure is approximately 42 mmHg and/or renal resistance is approximately 1.39, the flow rate to the kidney can be approximately 30 mL/min. In some embodiments, when pressure is approximately 30-50 mmHg and/or renal resistance is approximately 0.5-2.5, the flow rate to the kidney can be approximately 10-50 mL/min. In some embodiments, when pressure is between than 23 mmHg and 42 mmHg and/or renal resistance is between 0.16 and 1.55, the flow rate to the kidney can be between 30 and 130 ml/min. In some embodiments, when pressure is between than 5 mmHg and 75 mmHg and/or renal resistance is between 0.01 and 5, the flow rate to the kidney can be between 10 and 200 mL/min. In some embodiments, when pressure is less than 23 mmHg and/or renal resistance is less than 0.16, the flow rate to the kidney can be greater than or equal to 130 mL/min. In some embodiments, when pressure is less than 5-50 mmHg and/or renal resistance is less than 0.01-5, the flow rate to the kidney can be greater than or equal to 75-200 mL/min. In some embodiments, when pressure is approximately 23 mmHg and/or renal resistance is approximately 0.18, the flow rate to the kidney can be approximately 130 mL/min. In some embodiments, when pressure is approximately 5-50 mmHg and/or renal resistance is approximately 0.01-5, the flow rate to the kidney can be approximately 75-200 ml/min.

Renal resistance, or resistance of the cannulated vessel, can be determined by dividing the pressure at the flow regulator valve 48 by the flow rate into the biological sample. The flow regulator valve 48 can control flow to the biological sample, for example the renal artery of a kidney, based on the non-linear equation below.

$$P = A - BF - CF^2$$

In the equation above, P represents pressure at the flow regulator valve 48 and F represents flow rate into the biological sample. A, B, and C are constants. In one example, A can be 42.93, B can be 0.01076, and C can be 0.001072. In some examples, A can be between 35 and 45, B can be between 0.005 and 0.05, and C can be between 0.0005 and 0.0015. In some embodiments, A can be between 25 and 75, B can be between 0.00005 and 0.1, and C can be between 0.00005 and 0.1. In some embodiments, A can be between 10 and 100, B can be between 0.000005 and 1, and C can be between 0.000005 and 1. In some embodiments, the equation used to relate pressure at the flow regulator valve 48 to the flow rate into the organ can be binomial or polynomial.

In some examples, the flow regulator valve 48 can be set to control flow rate into the organ based on the equation above by choosing a valve with a particular cracking pressure threshold. One of skill in the art will understand that a cracking pressure threshold can be the minimum pressure required to open the valve and allow fluid or gas flow. The cracking pressure threshold can be the point at which the valve begins to open and initial resistance is overcome, such that a minimum amount of fluid is released from the fluid channel. The cracking pressure threshold can correspond to the pump speed such that the flow rate into the organ corresponds to the equation described herein. The flow regulator valve 48 in this embodiment can be based on a pump with a speed of 130 mL/min. The flow regulator valve 48 in this embodiment can be based on a pump with a speed of 100-150 mL/min. The flow regulator valve 48 in this embodiment can be based on a pump with a speed of 50-200 mL/min. The flow regulator valve 48 in this embodiment can be based on a pump with a speed of 10-500 mL/min. The flow regulator valve 48 can be a spring-loaded ball check valve, for example with a single ball, in which the spring allows preservation fluid to escape the fluid circuit into the organ chamber 17 when pressure is above the cracking pressure threshold. This pressure increase can be caused by arterial resistance, such as renal resistance, slowing flow into the organ and causing build up in the valve. Once cracking pressure is reached, higher pressures can cause the spring to constrict non-linearly, causing the flow from the flow regulator valve 48 to the organ chamber 17 to be non-linear in relation to the renal resistance. Because flow from the flow regulator valve 48 to the organ chamber 17 is non-linear in this case, the flow from the flow regulator valve 48 to the organ can also be non-linear in relation to the renal resistance, based on the amount of fluid exiting the fluid circuit. In certain examples, the use of the flow regulator valve 48 can allow the constant pump to be effective throughout transport by controlling the flow rate into the organ based on the renal resistance. The flow rate caused by the flow regulator valve 48 can be enhanced or even optimal, such that the flow does not damage the artery by overcoming resistance too harshly nor does the flow rate allow too little flow in when renal resistance would allow more flow without causing damage.

The flow rate to the kidney can be determined based on the pressure and/or the renal resistance in Table 1, below. The pressure measurements in Table 1 can be within approximately 5 mmHg. The renal resistance values in Table 1 can be within approximately 15%. The flow rate measurements can be within approximately 5 mL/min.

TABLE 1

| Pressure (mmHg) | Flow Rate (mL/min) | Renal Resistance (mmHg * min/mL) |
|---|---|---|
| >42 | ≤30 | >1.55 |
| 42 | 30 | 1.39 |
| 41 | 35 | 1.18 |
| 40 | 45 | 0.90 |
| 39 | 55 | 0.71 |
| 38 | 60 | 0.64 |
| 37 | 70 | 0.53 |
| 36 | 75 | 0.48 |
| 35 | 80 | 0.44 |
| 34 | 85 | 0.40 |
| 33 | 90 | 0.37 |
| 32 | 95 | 0.34 |
| 31 | 100 | 0.31 |
| 30 | 105 | 0.29 |
| 29 | 110 | 0.26 |
| 28 | 115 | 0.24 |
| 27 | 118 | 0.23 |
| 26 | 120 | 0.22 |
| 25 | 125 | 0.20 |
| 24 | 128 | 0.19 |
| 23 | 130 | 0.18 |
| <23 | ≥130 | <0.16 |

In some examples, the temperature sensor 50 can be configured to measure the temperature of the organ chamber 17. The temperature sensor 50 can be positioned on the bottom of the inner lid 40. When the canister 38 is filled with fluid, the fluid can contact the temperature sensor 50. The temperature sensor 50 can measure the temperature of the preservation fluid. In alternate embodiments, the temperature sensor 50 can be positioned on the organ rest 18, in the pumping chamber 16, on the outer tube 36, on the cannula receiver 20, or on the bottom of the inner lid 40 above the biological sample T. The temperature of the biological sample T can be measured directly by the temperature sensor 50 or indirectly based on the temperature measurement of the fluid. The temperature sensor 50 can communicate the measurement to an external device or a display on the device.

In some examples, a pressure sensor 52 and pressure dampener 54 can be positioned near the tube 36, for example within the inner lid 40. The pressure sensor 52 can measure the pressure of the fluid in the fluid channel. The pressure sensor 52 can be in-line with the perfusion circuit. The pressure sensor 52 can be connected to the pressure dampener 54. The pressure dampener 54 can have three openings. Two openings of the pressure dampener 54 can be connected to the fluid circuit and one opening of the pressure dampener can be connected to the pressure sensor 52. The pressure dampener 52 can include a mechanism to reduce pulsation caused by the pump. The pressure sensor 52 can communicate the measurement to an external device or a display on the device. The pressure dampener 54 can be a pulsation dampener that reduces the pulsation caused by the pump. The apparatus 10 can include a cooling element, for example eutectic cooling packs, in proximity to the biological sample T.

In certain examples, the apparatus 10 can be a canister 38 and lid 40 contained inside an outer canister 138 and outer lid 140. The apparatus 10 can be contained inside a shipper as described with respect to FIGS. 4A and 4B. The apparatus 10 can be made of plastic, for example polycarbonate.

In some examples, the apparatus 10 can be used to perfuse a liver. In some examples, the organ can be perfused via the portal vein and hepatic artery. In some examples, the organ can be perfused via the portal vein only. In some examples, the organ can be perfused using a barbed or straight cannula.

Figure 2A:
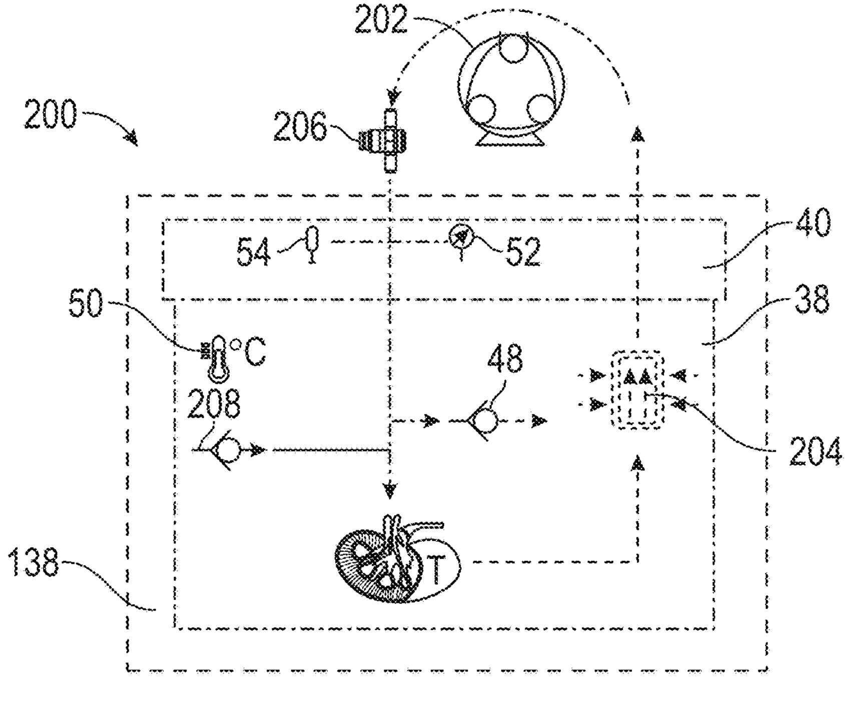
FIG. 2A is a diagram of an example perfusion circuit for perfusing a biological sample.
Figure 2B:
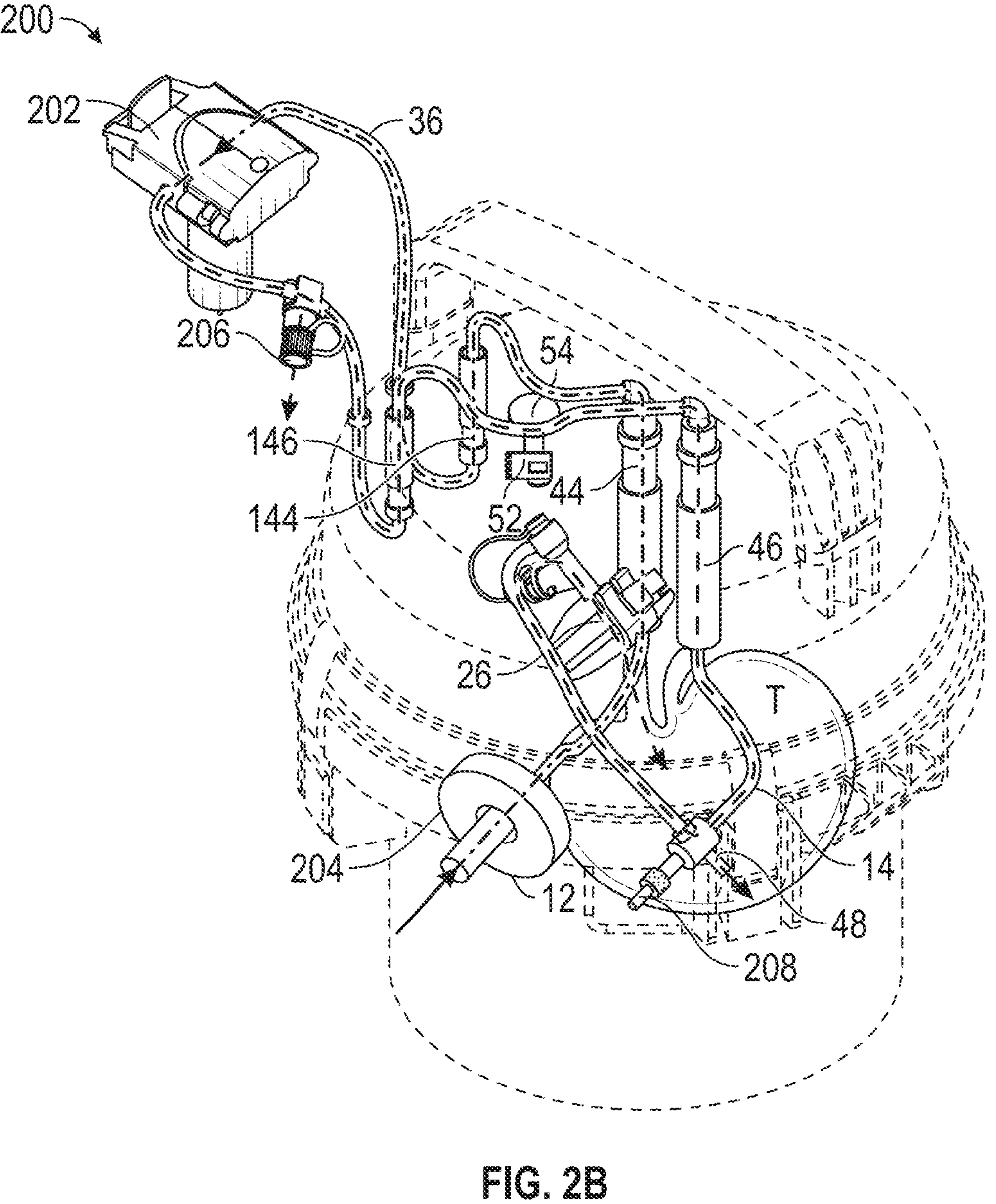
FIG. 2B is a schematic of the example perfusion circuit for perfusing a biological sample of FIG. 2A.

FIG. 2A is a diagram of an example perfusion circuit 200 for perfusing a biological sample T. FIG. 2B is a schematic of the example perfusion circuit 200 for perfusing a biological sample T of FIG. 2A.

In some examples, the pump 202 can facilitate flow of the preservation fluid. The pump 202 can be a peristaltic pump in contact with the outer tube 36. The pump 202 can be positioned on the shipper, as described with respect to FIGS. 4A and 4B. As the peristaltic pump 202 rolls in contact with the flexible outer tube 36, the force applied to the outer tube 36 can cause fluid to flow through the perfusion circuit 200. This can cause the inlet 12 to draw fluid from the pumping chamber 16. The pump 202 can be a small footprint flip-top pump. A user can thread the tube 36 into the pump 202.

In certain examples, a fluid filter 204 can filtrate the fluid. The fluid filter 204 can be an in-line filter at the pump inlet 12 or in the fluid channel between the inlet 12 and the cannula receiver 20. In some embodiments, the filter 204 can be at another point in the fluid channel. The fluid filter can be a 20-micron stainless steel filter in a polyethylene housing.

As shown with respect to FIG. 2B, the inlet 12 can take in fluid from the organ container 38. Fluid can flow from the inlet 12 to the outer tube 36 in contact with the pump 202, for example by traveling through the lid inlet 44 and the outer canister inlet 144. Fluid can then flow from the outer tube 36 to the outlet 14, for example through the lid outlet 46 and the outer canister outlet 146. Fluid can flow from the outlet 14 to cannula 26 and/or the flow regulator valve 48, depending on the renal resistance. Fluid can flow from the cannula 26 to the biological sample T, and then from the biological sample T into the storage chamber 17. As the peristaltic pump 202 rolls, it can enact force on the outer tube 36 in a pulsatile manner. The pressure dampener 54 can cause flow through the perfusion circuit 200, or fluid circuit, to become more smooth or constant as opposed to pulsatile. In some examples, the perfusion circuit 200 can perfuse the organ in a pulsatile manner. For example, the pulsatile perfusion may involve repeated perfusion cycles with a period of time in between.

In certain examples, an operator can remove fluid, for example gas, from the perfusion circuit 200 at the purge point 206. The operator can use a syringe, for example, to draw fluid from the purge point 206. The one-way valve 208 can allow preservation fluid from the canister 38 to backfill the perfusion circuit 200 when fluid is drawn out of the purge point 206. Advantageously, this can allow the perfusion circuit 200 to be purged of gas. The purge point 206 can prevent fluid from entering or exiting the perfusion circuit 200 when fluid is not being drawn out. The one-way valve 208 can prevent fluid from entering or exiting the perfusion circuit 200 when fluid is not being drawn out.

In some examples, the pump 202 can operate at a constant rate throughout transport. The pump 202 can operate independently of renal resistance. For example, the pump 202 can vary in speed based on hardware or software, but the pump may not change its speed based on the renal resistance or pressure in the perfusion circuit 200. The perfusion circuit 200 can be a closed loop such that the volume of preservation fluid is constant. Advantageously, the perfusion circuit 200 can operate continuously without intervention. A battery can power the pump 202 with a constant voltage. A battery can power the pump 202 with a voltage independent of renal resistance. Renal resistance can mean the arterial resistance or the resistance of a vessel of the biological sample.

Figure 3A:
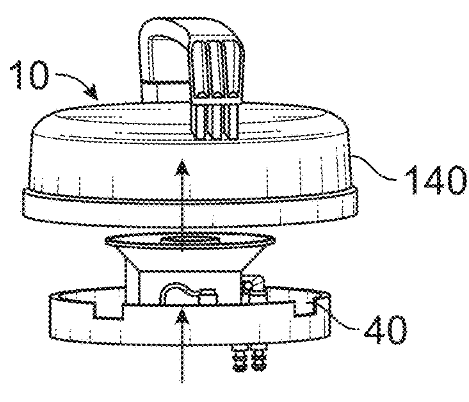
FIG. 3A shows an exploded view of an example of the outer lid, inner lid, inner canister, and inner canister.
Figure 3A:
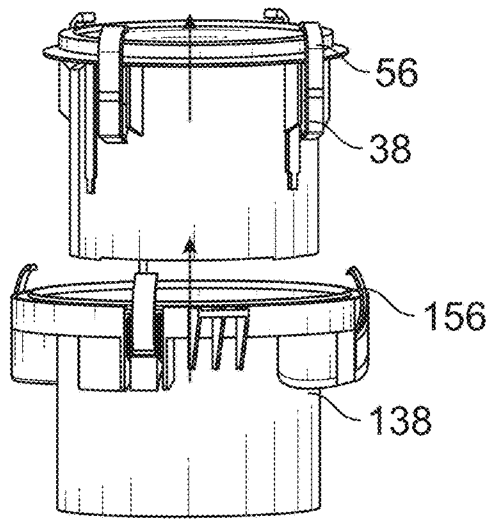
Figure 3B:
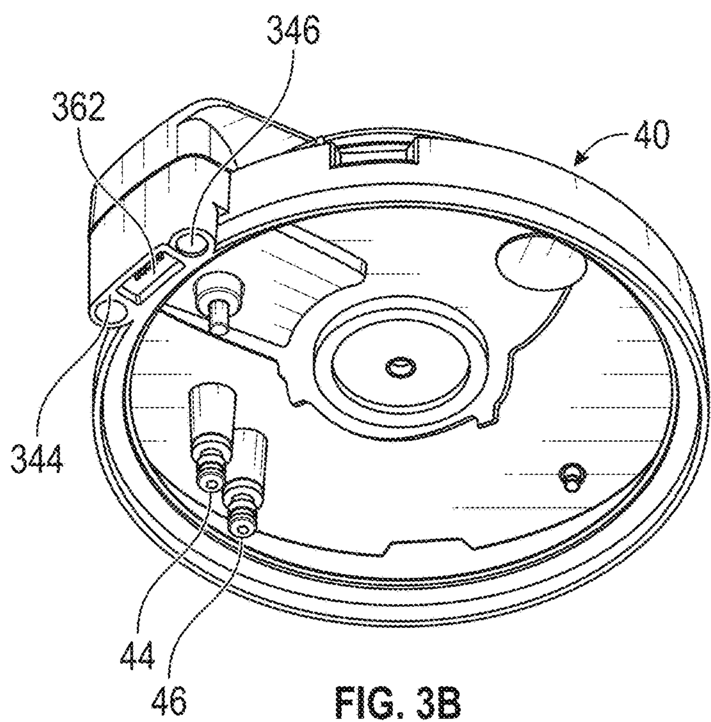
FIG. 3B shows a bottom perspective view of the example of the inner lid of FIG. 3A.
Figure 3C:
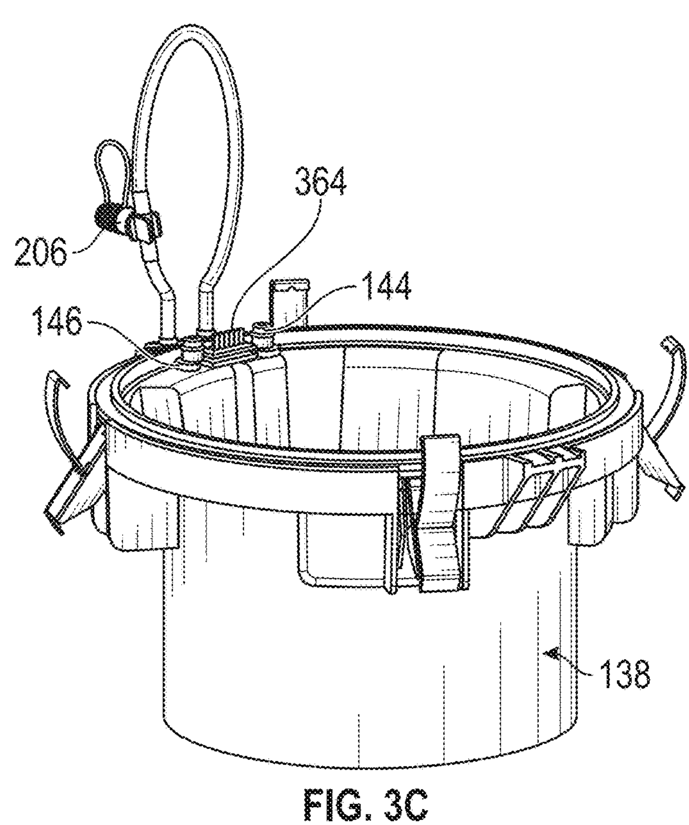
FIG. 3C illustrates the example of the outer canister of FIG. 3A.
Figure 3D:
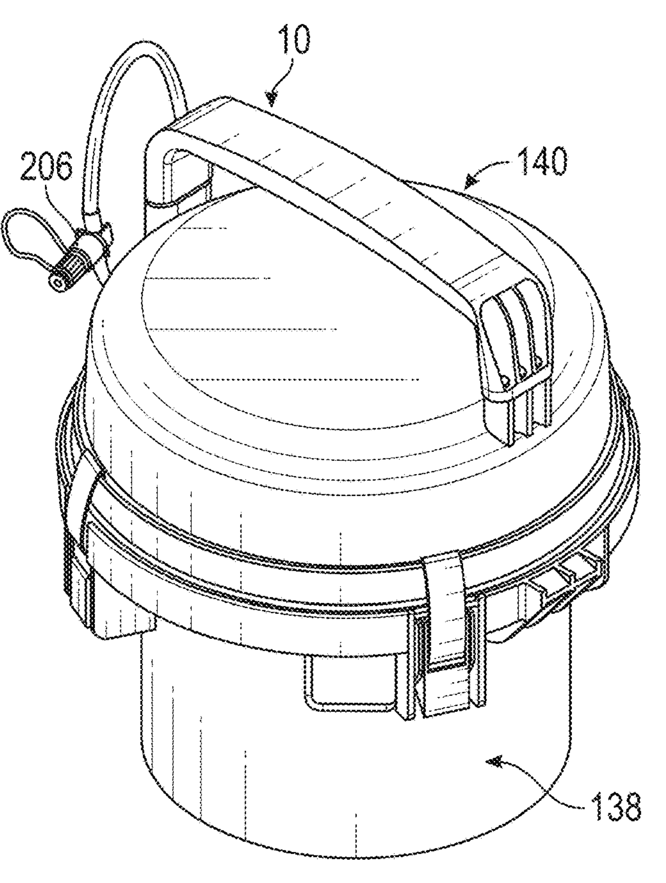
FIG. 3D illustrates the example of the outer canister and outer lid of FIG. 3A.

FIG. 3A shows an exploded view of an example of the outer lid 140, inner lid 40, inner canister 38, and outer canister 138. FIG. 3B shows a bottom perspective view of the example of the inner lid of FIG. 3A. FIG. 3C illustrates the example of the outer canister 138 of FIG. 3A. FIG. 3D illustrates the example of the outer canister 138 and outer lid 140 of FIG. 3A.

In some examples, the inner canister 38 can couple to the inner lid 40 such that the lid inlet 44 and lid outlet 46 couple with the inlet 14 and outlet 16, respectively. The clamps 56 can mechanically secure the inner canister 38 to the inner lid 40.

In some examples, the inner lid 40 can couple to the outer canister 138, for example after the lid 40 and the inner canister 38 have been coupled. The lid inlet 44 can be fluidically connected to the outer inlet connector 344. The lid outlet 46 can be connected to the outer outlet connector 346. The inner lid 40 can connect to the outer canister 138 such that the outer inlet connector 344 connects to the outer canister inlet 144 and the outer outlet connector 346 connects to the outer canister outlet 146. The electrical connector 364 on outer canister 138 can connect to the electrical receiver 362 on the inner lid 40. The electrical receiver 362 can be positioned between the outer inlet connector 344 and the outer outlet connector 346. The electrical connector 364 can be positioned between the outer canister inlet 144 and the outer canister outlet 146.

As shown in FIG. 3D, the outer canister 138 can couple with the outer lid 140. The clamps 156 can mechanically secure the outer canister 138 to the outer lid 140. The purge point 206 can have a cap to prevent fluid from exiting the circuit. The outer canister 138 and outer lid 140 can protect the apparatus 10 from the environment, ensuring that the biological sample remains sterile.

Figure 4A:
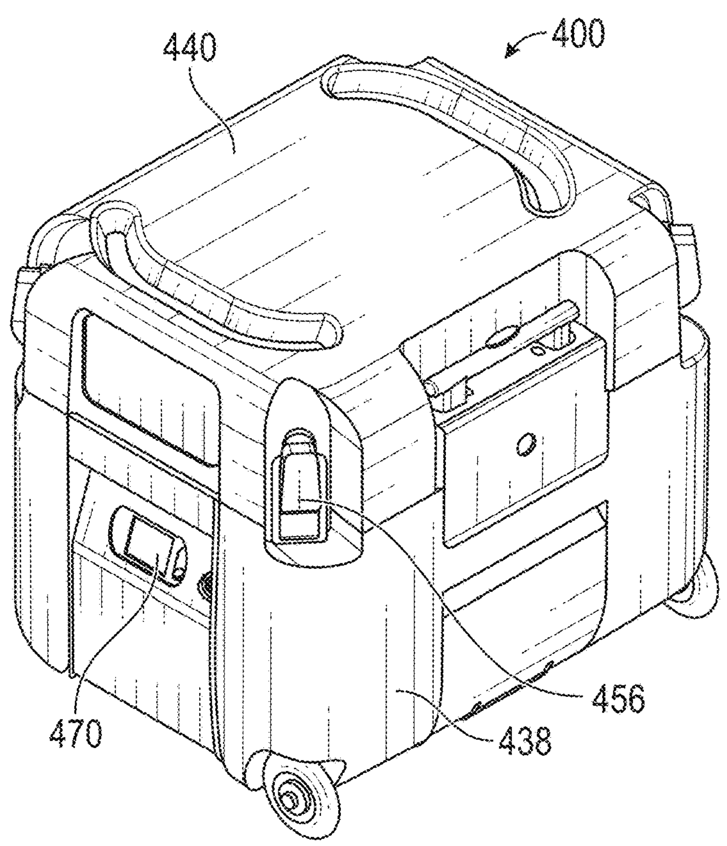
FIG. 4A illustrates an example of a transporter for the apparatus of FIG. 1C.
Figure 4B:
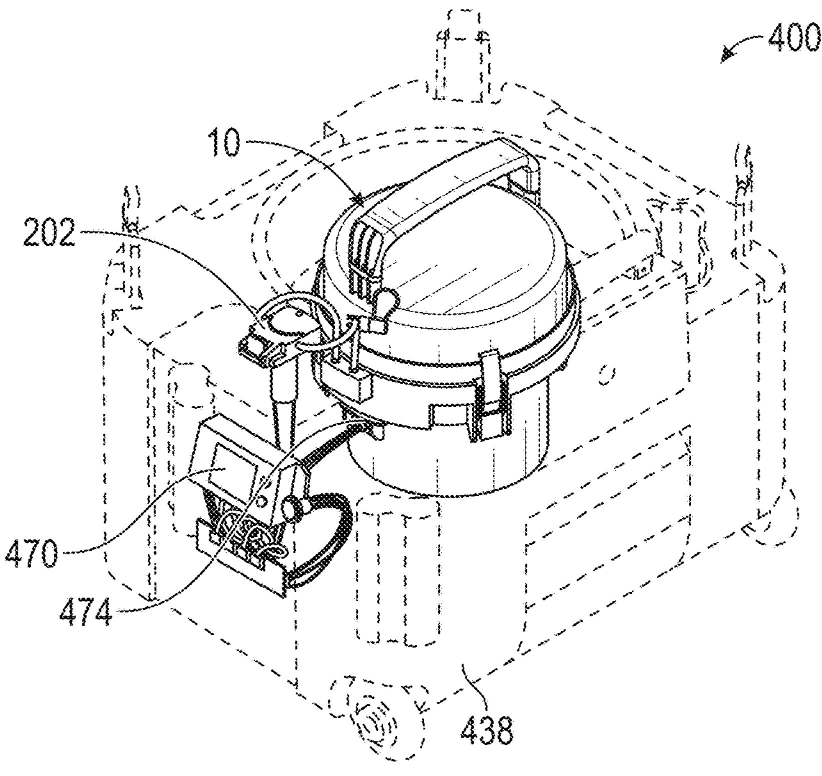
FIG. 4B illustrates the example of the transporter body of FIG. 4B with the transporter body partially transparent.

FIG. 4A illustrates an example of a transporter 400 for the apparatus 10. FIG. 4B illustrates the example of the transporter body 438 for the apparatus 10 of FIG. 4B with the transporter body 438 partially transparent.

The transporter 400 can have a transporter body 438 and a transporter lid 440. In some examples, the transporter lid 440 can be coupled to the transporter body and mechanically secured using clamps 456. The pump 202 can be positioned on the transporter body 438. The pump 202 can operate at 7.2 V. In some embodiments, the pump 202 can operate at 1-10 V. In some embodiments, the pump 202 can operate at 1-20 V. The battery in the transporter 400 can supply the voltage at which the pump 202 operates. The transporter can include a button or switch for turning the pump 202 on and off. The pump 202 can generate a flow rate of approximately 130 mL/min. In some embodiments, the pump 202 can generate a flow rate of 110-150 mL/min. In some embodiments, the pump 202 can generate a flow rate of 80-180 mL/min. In some embodiments, the pump 202 can generate a flow rate of 50-200 mL/min. Advantageously, the use of a battery at approximately 7.2 V, or within the disclosed ranges, to power the pump 202 with a flow rate of approximately 130 mL/min, or within the disclosed ranges, can efficiently perfuse the organ.

In certain examples, the transporter 400 can have a handle and wheels to facilitate transport. The handle can be a telescoping handle. The transporter 400 can include a left and right lifting handle for lifting the shipper during transportation. The transporter 400 can include a lock-ring for securing the apparatus 10 in place during transportation. The transporter 400 can include an electrical connector 474 for connection to the apparatus. The electrical connector 474 can connect the apparatus 10 to the display 470.

In certain examples, the display 470 can include a datalogger. The display 470 can display temperature within the canister 38, ambient temperature, pressure within the fluid circuit, battery voltage, and/or other parameters. The display 470 can be connected to the apparatus 10 through wired or wireless connection. The display 470 can be connected to the temperature sensor 50 and/or the pressure sensor 52. The transporter 400 can include a battery or power source connected to the display 470 and/or the pump 202.

The transporter 400 can contain cooling media to maintain the temperature of the biological sample. For example, the cooling media can be placed on top of the outer lid 140 and around the outer canister 138. The cooling media can include eutectic cooling blocks. The cooling media can have a temperature of 1° C. In some embodiments, the cooling media can have a temperature of 0.5-10° C. The organ can be transported at a temperature with an operating range of 4-8° C. In some embodiments, rgan can be transported at a temperature with an operating range of 2-10° C.

Cooling media can be positioned around the outer canister 138 and/or on top of the outer lid 140. The cooling media around the outer canister 138 can be ribbons of phase change material. The cooling media around the outer canister 138 can include five ribbons of phase change material. Three ribbons can be arranged radially around the outer canister 138 at or near the bottom of the outer canister 138. Two ribbons can be arranged radially around the top of the outer canister 138 and/or radially around the outer lid 140. In some examples, the cooling media around the outer canister 138 can include 1-10 ribbons of phase change material. In some examples, the cooling media around the outer canister 138 can include 1-20 ribbons of phase change material. The ribbon of phase change material can include individual phase change material packs that are linked together. The ribbons may be overlayed radially around other ribbons. In some examples, 1-5 ribbons can be arranged radially around the outer canister 138 at or near the bottom of the outer canister 138. In some examples, 1-10 ribbons can be arranged radially around the outer canister 138 at or near the bottom of the outer canister 138. In some examples, 1-5 ribbons can be arranged radially around the top of the outer canister 138 and/or radially around the outer lid 140. In some examples, 1-10 ribbons can be arranged radially around the top of the outer canister 138 and/or radially around the outer lid 140.

The cooling media on top of the outer lid 140 can be a pouch of phase change material. The pouch of phase change material can contain four individual phase change material envelopes. In some examples, the pouch of phase change material can contain 2-6 individual phase change material envelopes. In some examples, the pouch of phase change material can contain 1-10 individual phase change material envelopes. The pouch of phase change material can be positioned under the handle of the outer lid 140. In some examples, the phase change material can have a temperature of 1° C., 2° C., 3° C., 4° C., 5° C., 6° C., 7° C., or 8° C.

In some examples, the transporter 400, or shipper, can be made of plastic or a polymer, for example rigid, molded expanded polystyrene.

FIGS. 5A-5D illustrate an example of an accumulation chamber 500. The accumulation chamber 500 can compensate for fluid expansion within the canister 38 due to external pressure changes. The accumulation chamber 500 can include a top portion 582, a bottom portion 584, and a balloon 586 between the top portion 582 and the bottom portion 584.

The balloon 586 can expand when fluid in the canister 38 expands due to high external pressure and contract when fluid in the canister contracts due to low external pressure. This is advantageous as it can allow the canister 38 to respond to changes in external pressure. The canister 38 can be filled with preservation fluid, so forces acting on the canister, transporter, or apparatus can cause the preservation fluid to expand. Without an accumulation chamber 500, this could affect the perfusion of the organ. If the apparatus is jostled during transport or transported at an altitude that results in a pressure change, the accumulation chamber 500 can prevent the internal pressure from significantly changing, thus protecting the organ.

In some examples, the balloon 586 can be made of urethane. In some embodiments, the balloon 586 can be a flexible membrane or a series of flexible membranes. A space between the flexible membranes or between a flexible membrane and the top portion 582 or the bottom portion 584 of the accumulation chamber 500 can expand and contract in response to external pressure changes.

In some examples, the top portion 582 and bottom portion 584 can be made of plastic, for example the same plastic used in the apparatus 10 of FIG. 1A-C. The top portion 582 can have apertures 588 to allow the balloon 586 to expand. The top portion 582 and bottom portion 584 can limit how much the balloon 586 expands. The top portion 582 can couple to the bottom portion 584 using clips 589.

In some examples, the bottom portion 584 can have an accumulation chamber connector 587. The accumulation chamber connector 587 can seal to the apparatus 10, for example the fill port 28 and/or the vent port 30 of the inner lid 40. The accumulation chamber connector 587 can be in fluid communication with the balloon 586.

Figure 5A:
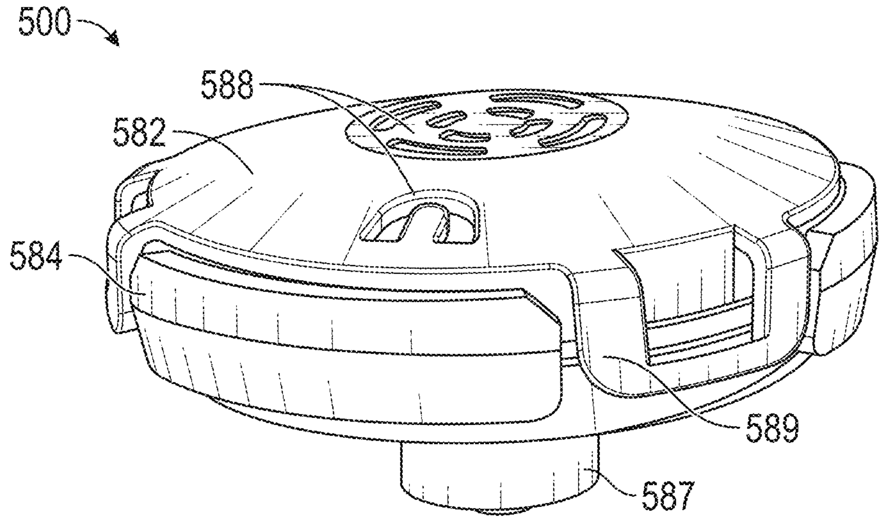
FIGS. 5A-5D illustrate an example of an accumulation chamber.
Figure 5B:
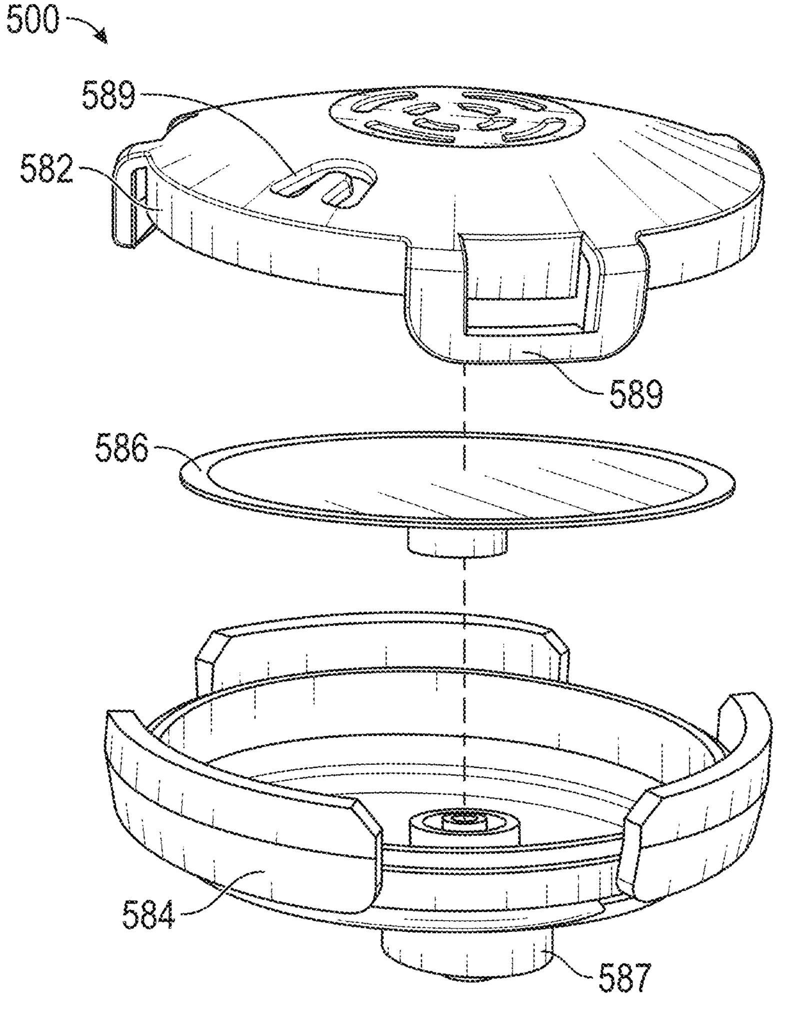
Figure 5C:
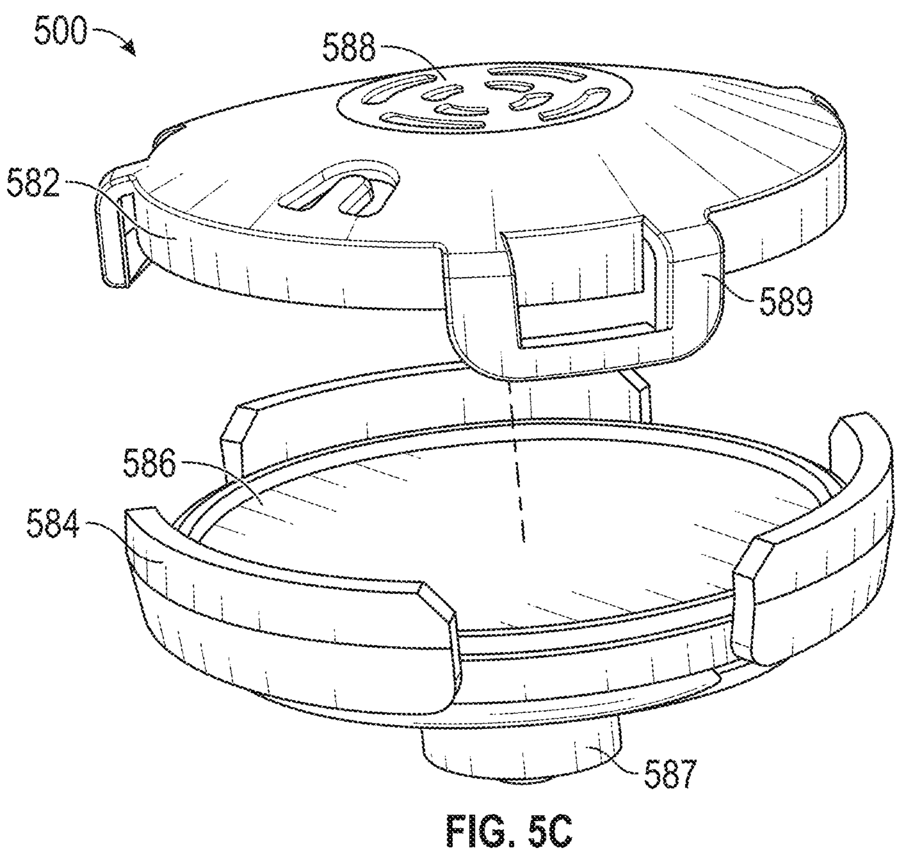
Figure 5D:
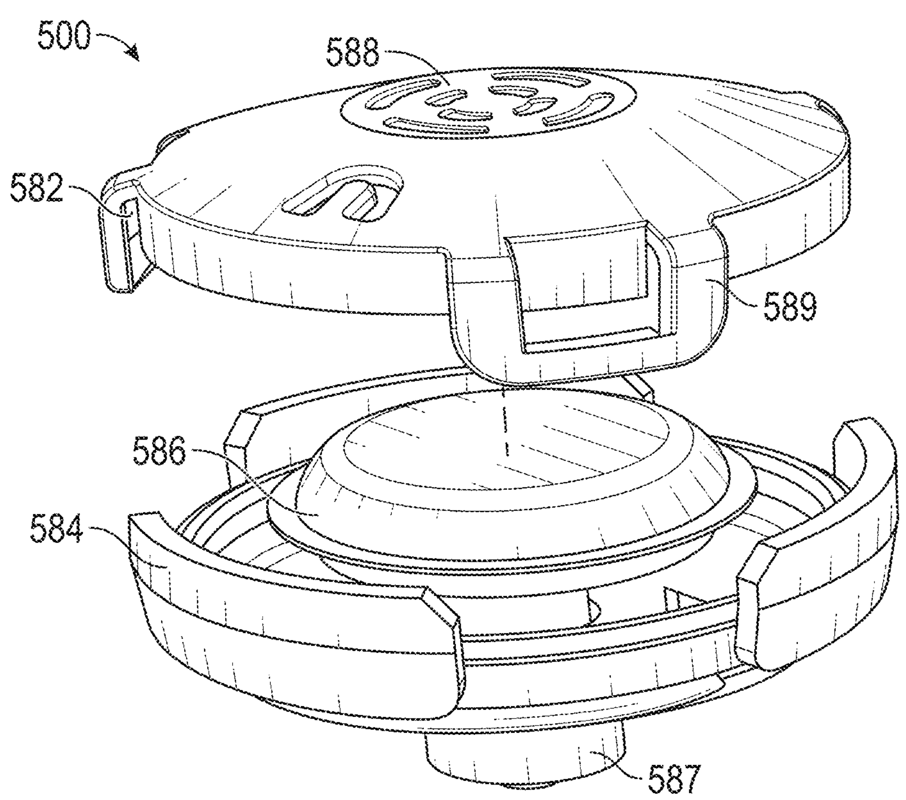
Figures 6A, 6B:
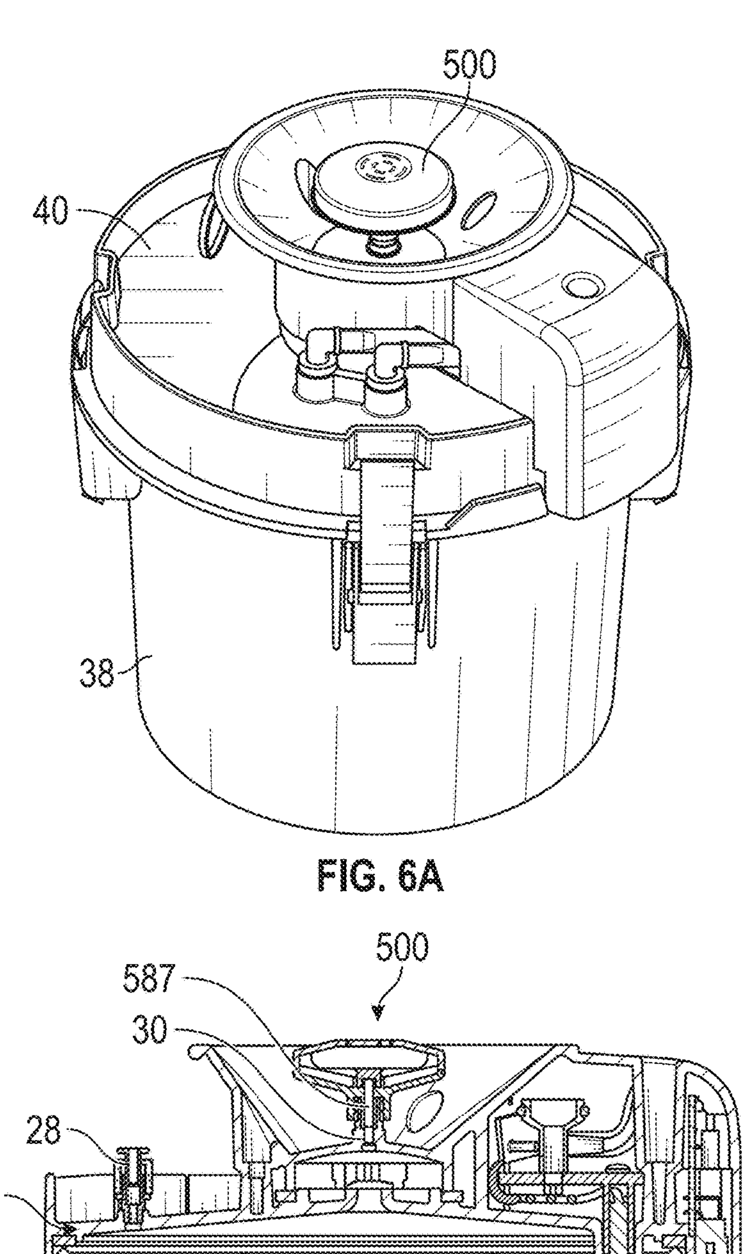
FIGS. 6A and 6B illustrate the example of the accumulation chamber of FIG. 5A on the vent port of the apparatus of FIG. 1C.

FIGS. 6A and 6B illustrate the example of the accumulation chamber 500 of FIG. 5A on the vent port 30 of the apparatus 10.

In certain examples, the accumulation chamber 500 can be positioned on the fill port 28 and/or the vent port 30. The accumulation chamber 500 can be in fluid communication with the interior of the canister 38. In some embodiments, the fill port 28 and vent port 30 can be sealed with caps and/or balloons. Advantageously, the accumulation chamber 500 allows some expansion of the fluid in the canister 38 to maintain pressure, but does not allow significant changes in volume of the canister 38 or density of the fluid.

FIG. 7A illustrates an example of an organ rest 718 with posts 790 and an organ retainer 792.

The organ rest 718, or kidney rest, can be similar to the organ rest 18 of FIG. 1A-C. In some examples, the posts 790 can be notched posts. The retainer 792 can have attachment mechanisms 794 that can fit along the notches. The retainer 792 can be moved up and down along the posts 790 to adjust for the size of the biological sample T. The retainer 792 can be locked in place once a desired height is determined, for example by sliding the retainer such that the attachment mechanisms 794 engage the notches. The retainer 792 can be couplable with the posts 790 at various points.

In some examples, the retainer 792 can have a plurality of straps configured to keep the biological sample T from moving horizontally and/or vertically. The straps can be made of rubber, plastic, or polymer. The straps can be curved to accommodate the shape of the biological sample T.

FIG. 7B illustrates a side view of the example of the organ rest 718 of FIG. 7A. FIG. 7C illustrates a top view of the example of the organ rest 718 of FIG. 7A.

In some examples, the organ rest 718 can include a groove 721. A cannula receiver 720, or organ adapter, can be slidable along the groove 721. The cannula receiver 720 can lock in place along the groove 721, for example by securing pins fixed to the cannula receiver 720 at a position along recesses around the groove 721. A user can lock the cannula receiver 720 in a position such that an artery of the biological sample, for example a renal artery of a kidney, is in tension when the biological sample is cannulated or otherwise attached to an adapter. The cannula receiver 720 can be pulled out to a position in which the cannula receiver 720 can slide along the groove 721 and pushed into a position in which the cannula receiver 720 is locked in place.

Figure 8A:
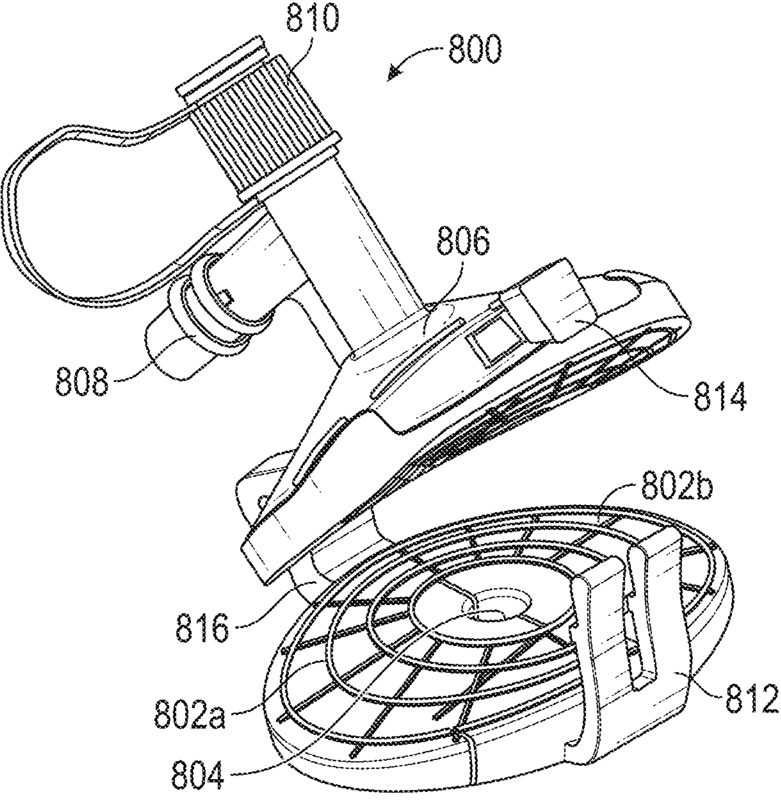
FIG. 8A illustrates an example of a round-hole cannula in an open configuration.
Figure 8B:
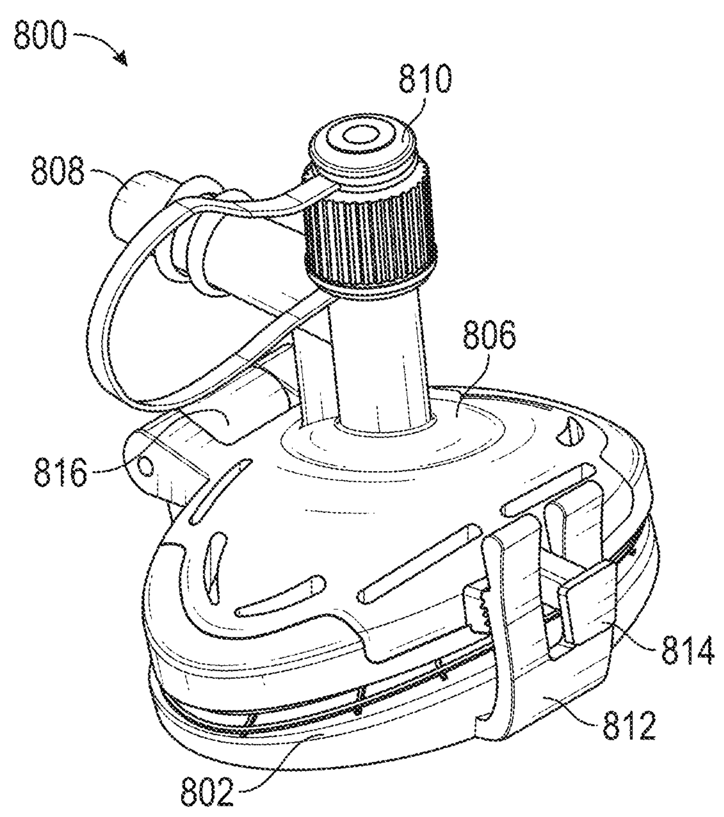
FIG. 8B illustrates the example of the round-hole cannula in a closed configuration.

FIG. 8A illustrates an example of a round-hole cannula 800 in an open configuration. FIG. 8B illustrates the example of the round-hole cannula 800 in a closed configuration.

The cannula 800 can be configured to seal to the artery, for example a renal artery. In some examples, the cannula 800 can include a base portion 802. The base portion 802 can be divided into two portions, a first base portion **802*a* and a second base portion 802*b*. The second base portion 802*b* can be a slider portion that slides away from the first base portion 802*a* to allow the vessel to be more easily pulled through the central aperture 804. The second base portion 802*b*, or slider portion, can slide toward the first base portion 802*a* to keep the vessel from moving significantly during transportation without sealing the vessel entirely in place. The first base portion 802*a* can be moved toward and away from the second base portion 802*b*. The base portions 802*a,b* can be moved away from each other to expand a central aperture 804 such that the vessel, artery, or artery cuff can be pulled through the central aperture 804. Then, the base portions 802*a,b* can be moved closer together once the artery is in place. The base portions 802*a,b* can be locked in place when they are sealed together. The base portions 802***a,b* can be crescent shaped components. Together, the base portions 802*a,b* can form a rectangle, for example a rectangle with rounded corners, or an oval. The central aperture 804 can be circular, rectangular, hexagonal, octagonal, or diamond-shaped. The first base portion 802*a* and second base portion 802*b* can include elastic guard portions between them that define the central aperture 804.

In some examples, a cap portion 806 can be connected to the base portion 802, for example by a hinge 816. The cap portion 806 can be sealed on top of the base portion 802 and the vein, artery, or artery cuff. When sealed, the cap portion 806 can be parallel with the base portion 802. The cap portion 806 can include a barb 808. The barb 808 can be configured to connect with the cannula receiver 20 of the apparatus 10 of FIG. 1A-C. The cap portion 806 can include a valve 810. The valve 810 can be covered, for example by a cap. The valve 810 can be used to deair the cannula once attached, for example using a syringe to remove fluid from the circuit. The cannula 800 can be deaired by connecting a syringe filled with liquid, for example perfusion solution, to the end of the barb 808, uncapping the valve 810, and pushing the liquid into the barb 808 until the liquid flows out of the valve 810. The cannula 800 can be made of plastic, such as copolyester with a silicone seal and gasket. The cap portion 806 can include a small elastic protrusion for keeping the vessel open.

In some examples, the top of the base portion 802 and the bottom of the cap portion 806 can have grooves to better grip the vessel, artery, or artery patch. The grooves on the top of the base portion 802 can align with the grooves on the bottom of the cap portion 806. The artery patch of the renal artery can be secured between the base portion 802 and the cap portion 806. In some examples, a flared or stretched out end of the vessel can be secured between the base portion 802 and the cap portion 806. The barb 808 can have ridges extending radially to lock it into the cannula receiver 20 of the apparatus 10 of FIG. 1A-C.

In some examples, the cannula 800 can have a clip 812 on the base portion 802. The clip 812 can mechanically secure the base portion 802 to the cap portion 806 by coupling with a lock portion 814 of the cap portion 806.

In certain examples, the central aperture 804 can be round or circular to match a lumen of a vein. For example, the round central aperture 804 can match a diameter of a single lumen artery. The round central aperture 804 can have a diameter of approximately 3 mm, 5 mm, 7 mm, or 9 mm. In some embodiments, the round central aperture 804 can have a diameter of approximately 1-20 mm.

Figure 9A:
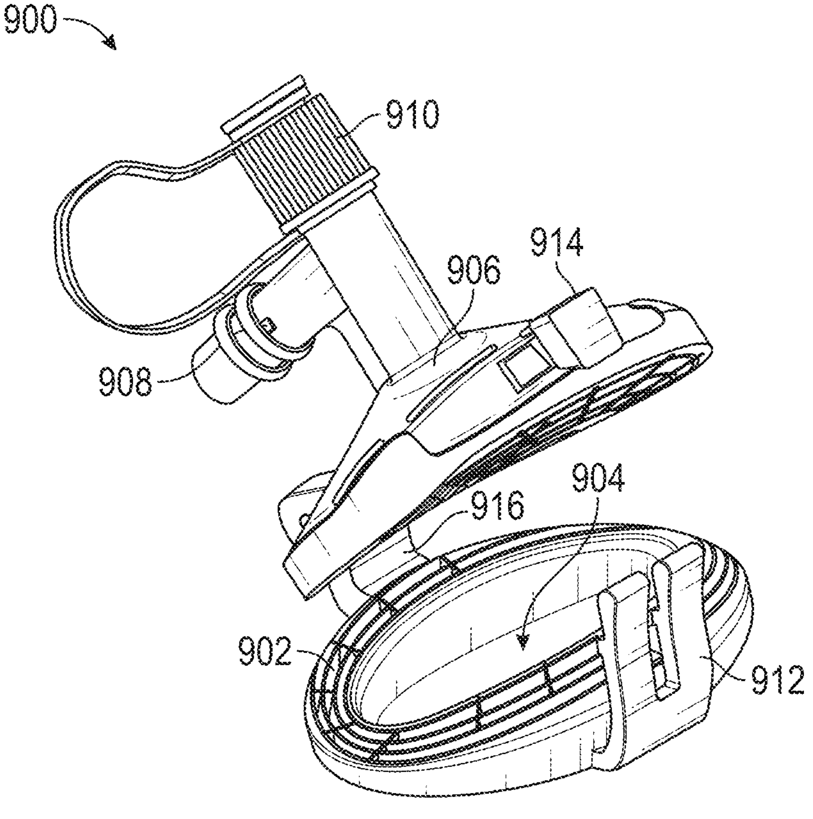
FIG. 9A illustrates an example of an oval-hole cannula in an open configuration.
Figure 9B:
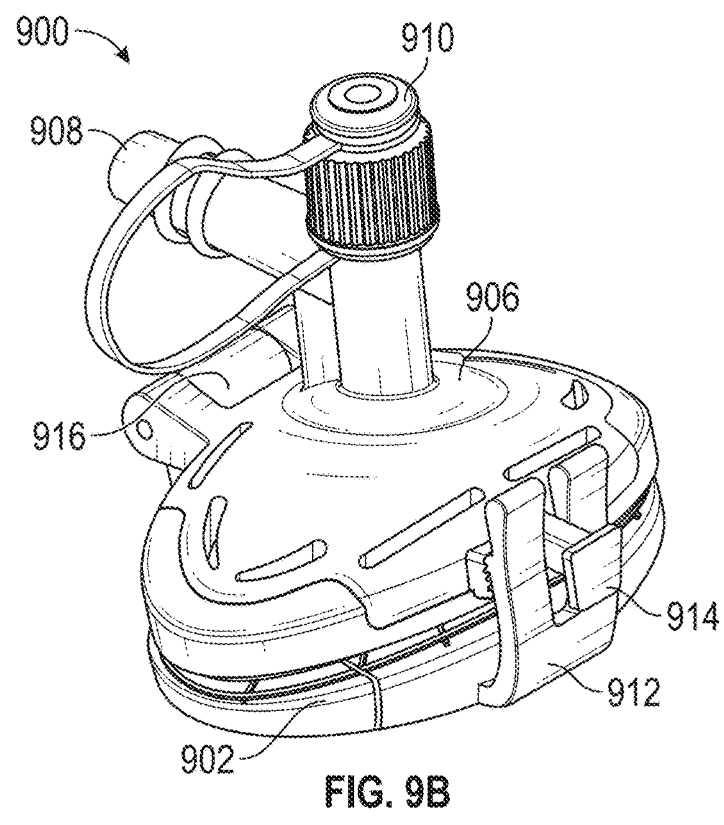
FIG. 9B illustrates the example of the oval-hole cannula in a closed configuration.

FIG. 9A illustrates an example of an oval-hole cannula 900 in an open configuration. FIG. 9B illustrates the example of the oval-hole cannula 900 in a closed configuration. The oval-hole cannula 900 can be similar to the cannula 800 of FIGS. 8A-B.

In some examples, the cannula 900 can be configured to seal to the artery, for example a renal artery. The cannula 900 can include a base portion 902. A vessel, artery, or artery cuff can be pulled through the central aperture 904. The base portion can be a rectangle, for example a rectangle with rounded corners, or an oval.

In some examples, a cap portion 906 can be connected to the base portion 902, for example by a hinge 916. The cap portion 906 can be sealed on top of the base portion 902 and the vein, artery, or artery cuff. When sealed, the cap portion 906 can be parallel with the base portion 902. The cap portion 906 can include a barb 908. The barb 908 can be configured to connect with the cannula receiver 20 of the apparatus 10 of FIG. 1A-C. The cap portion 906 can include a valve 910. The valve 910 can be covered, for example by a cap. The valve 910 can be used to deair the cannula once attached, for example using a syringe to remove fluid from the circuit. The cannula 900 can be made of plastic, for example copolyester with a silicone seal and gasket. The cap portion 906 can include a small protrusion for keeping the vessel open.

In some examples, the top of the base portion 902 and the bottom of the cap portion 906 can have grooves to better grip the vessel, artery, or artery patch. The grooves on the top of the base portion 902 can align with the grooves on the bottom of the cap portion 906. The artery patch of the renal artery can be secured between the base portion 902 and the cap portion 906. The barb 908 can have ridges extending radially to lock it into the cannula receiver 20 of the apparatus 10 of FIG. 1A-C.

In certain examples, the cannula 900 can have a clip 912 on the base portion 902. The clip 912 can mechanically secure the base portion 902 to the cap portion 906 by coupling with a lock portion 914 of the cap portion 906.

In some examples, the central aperture 904 can be ovular to match a lumen of a vein. For example, the oval central aperture 904 can match a diameter of a double lumen artery. The oval central aperture 904 can have dimensions of approximately 7 mm by 20 mm or 10 mm by 35 mm. In some embodiments, the oval central aperture 904 can have a width of approximately 1-20 mm. In some embodiments, the oval central aperture 904 can have a length of approximately 10-50 mm.

In some examples, once a kidney is recovered, an appropriately sized cannula can be connected to the renal artery. The cannula can be similar to those described with respect to FIGS. 8A-B or 9A-B. The cannula can have a clamshell design which is open when connecting the artery and is closed once the renal artery is placed. The artery or patch can be pulled through the aperture 804, 904 of the cannula using forceps. Once pulled through and seated, the cannula can be closed by snapping the cap portion 806, 906 and base portion 802, 902 together. The cannula can be de-aired by flushing cold preservation solution through the cannula and kidney using the barb 808, 908, or perfusion port on the cannula. This can be followed by checking for leaks. The kidney can then be placed in the organ container. The canulated kidney can be connected to the fluid circuit within the canister by pressing the valve 810, 910, or infusion port, into the cannula receiver. The slider of the cannula receiver can be adjusted up or down as necessary to assure there is little or no tension placed on the renal artery.

Figure 10:
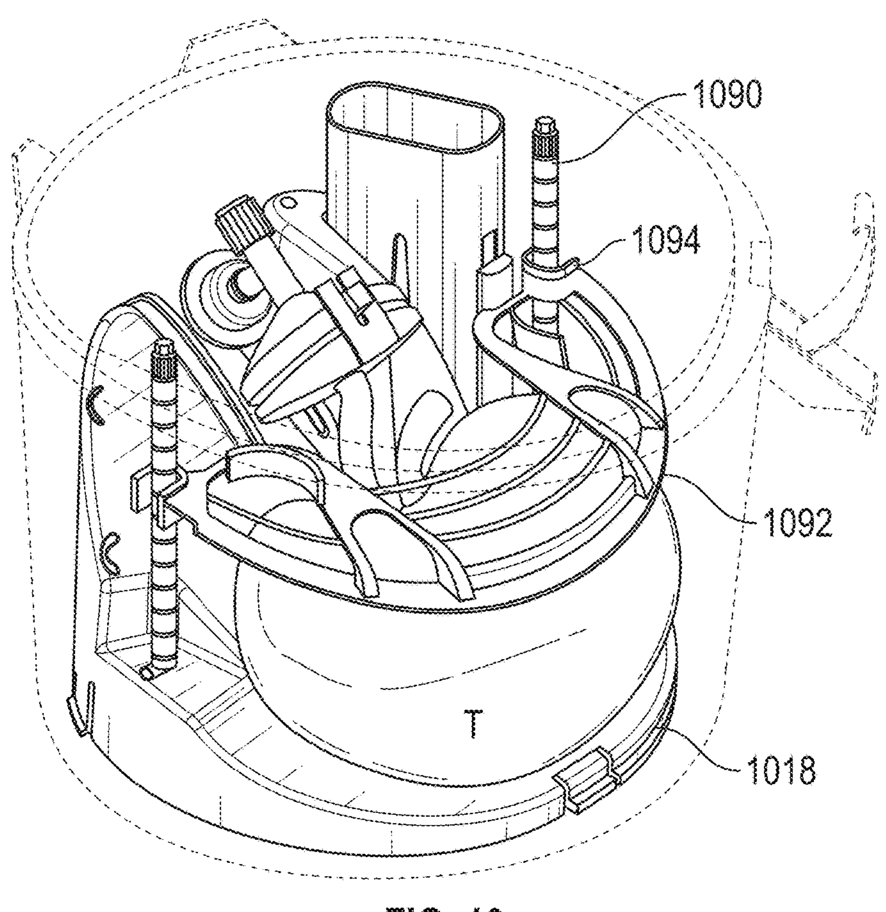
FIG. 10 shows an example of an organ retainer.

FIG. 10 shows an example of an organ retainer 1092. The organ retainer 1092 can be similar to the organ retainer in FIG. 7A. The organ retainer 1092 can be secured to organ posts 1090 using attachment mechanisms 1094. The organ can be positioned on an organ rest 1018.

The organ retainer 1092 can include curved members that conform to the shape of the organ. The curved members can be positioned on top of and in contact with the organ to prevent movement of the organ during transportation. In some examples, the organ retainer 1092 can be flexible or elastic. The organ retainer 1092 can deform to maximize contact with the organ. Advantageously, the elasticity of the organ retainer 1092 can allow the organ to be securely retained in place during transportation with reduced risk of damage to the organ.

Figure 11:
FIG. 11 is a graph of kidney pressure and vascular resistance in an example of the organ preservation device described herein.
Figure 11:
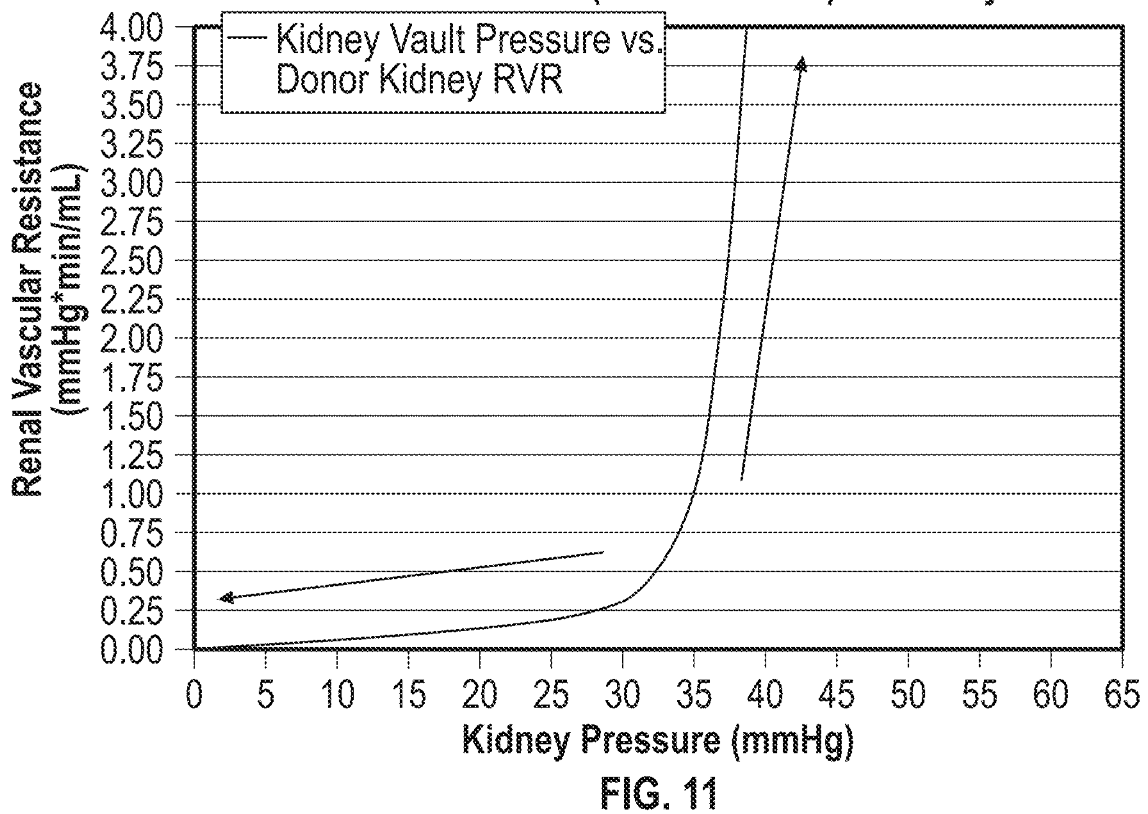

FIG. 11 is a graph of kidney pressure and vascular resistance in an example of the organ preservation device described herein.

The renal vascular resistances (RVR) shown in the graph are between 0 and 4 mmHg*min/mL. These RVR values are based on 325 deceased donor kidneys at 30 minutes, 1 hour, 2 hours, 4 hours, and at the end of perfusion. At 30 minutes, the mean RVR was 0.28 [0.04, 3.83]. At 30 minutes only three of the 325 kidneys had an RVR above 1.5. At the end of perfusion, the mean RVR was 0.17 [0.02, 1.10].

At a lower RVR, the kidney was observed to be more vasodilated. More flow went through the donor kidney and less flow diverted through the flow regulator valve. The perfusion pressure decreased.

At a higher RVR, the kidney was observed to be constricted. Less flow went through the donor kidney and more flow diverted through the flow regulator valve. The perfusion pressure increased.

Figure 12:
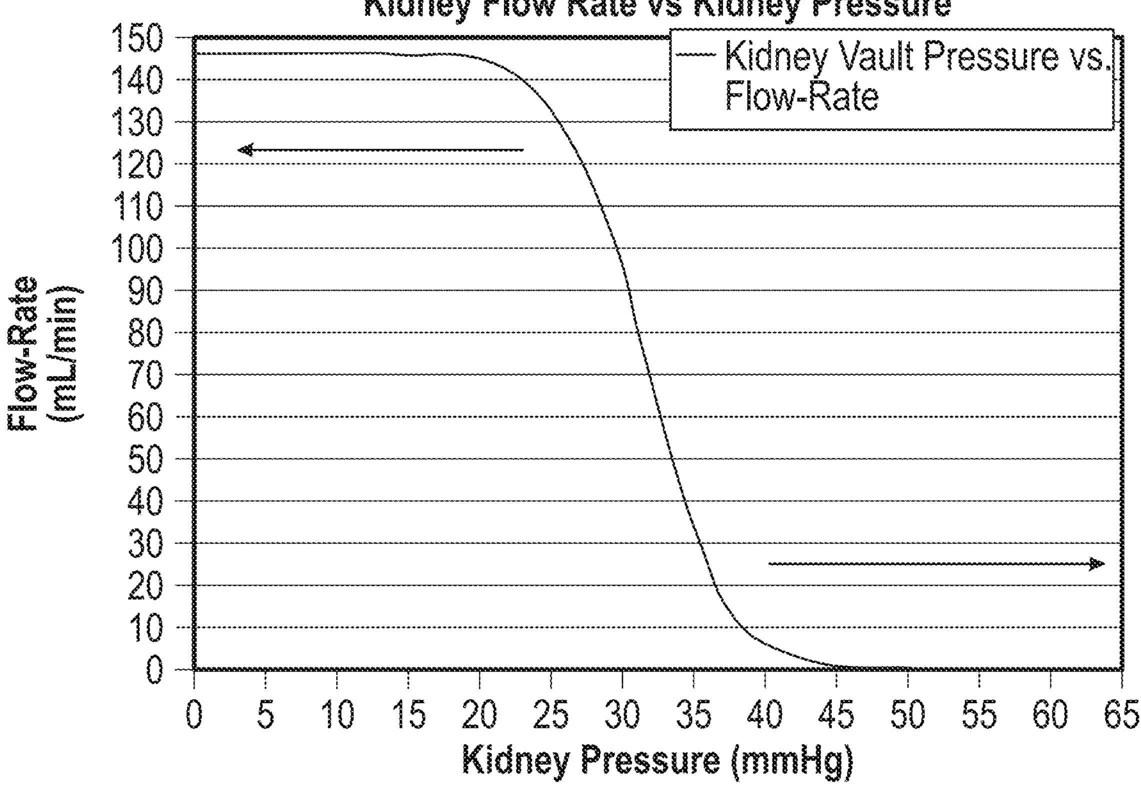
FIG. 12 is a graph of kidney pressure and perfusion flow in an example of the organ preservation device described herein.

FIG. 12 is a graph of kidney pressure and perfusion flow in an example of the organ preservation device described herein.

The perfusion pressure range was between 0 (for an RVR of 0) and 50 mmHg (for a fully occluded donor kidney).

Perfusion pressure was lower as the donor kidney vasodilated. More flow went into the donor kidney and less flow diverted through the flow regulator valve.

Perfusion pressure was higher when the donor kidney was constricted. Less flow went through the kidney and more flow diverted through the flow regulator valve.

Figure 13A:
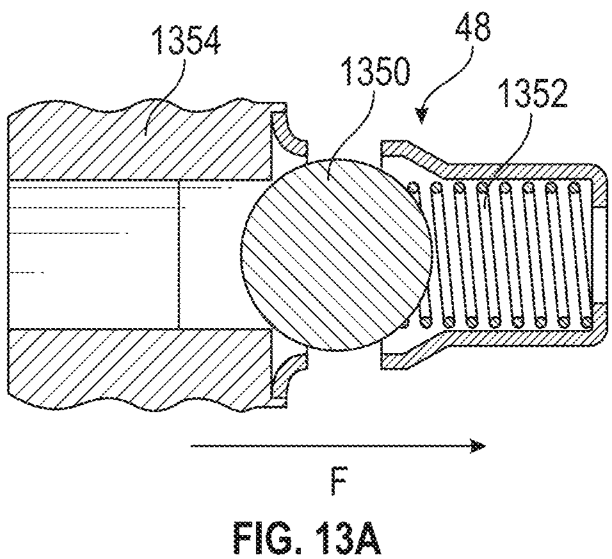
FIG. 13A shows an example of a flow regulator valve in the closed configuration.
Figure 13B:
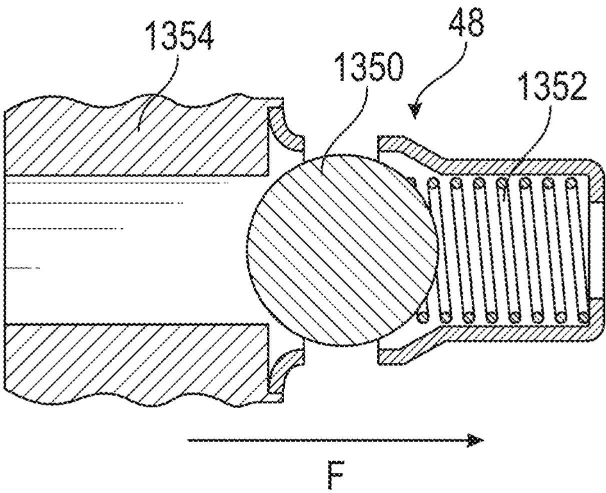
FIG. 13B shows the example of the flow regulator valve of FIG. 13A in the partially open configuration.
Figure 13C:
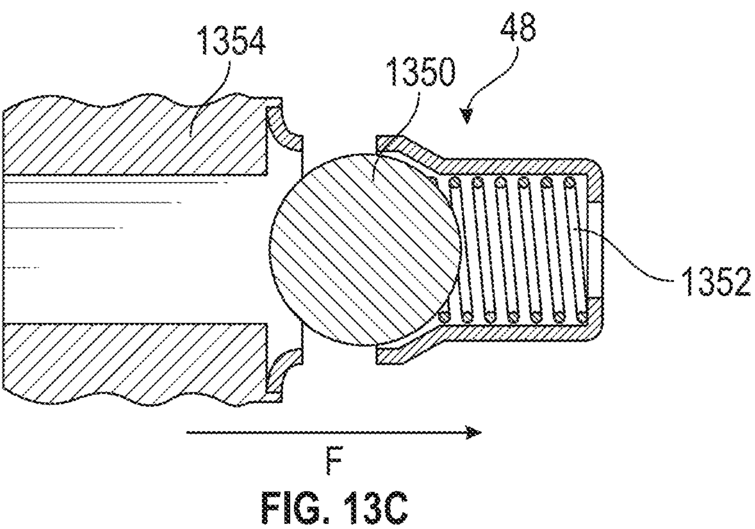
FIG. 13C shows the example of the flow regulator valve of FIG. 13A in the open configuration.

FIG. 13A shows an example of a flow regulator valve 48 in the closed configuration. FIG. 13B shows the example of the flow regulator valve 48 of FIG. 13A in the partially open configuration. FIG. 13C shows the example of the flow regulator valve 48 of FIG. 13A in the open configuration.

In some examples, the flow regulator valve 48 can mechanically open and close to varying degrees based on the pressure within the circuit. During operation, the flow regulator valve 48 can passively and progressively open and close in direct response to the pressure within the circuit. When pressure within the circuit is higher (due to higher RVR), the flow regulator valve 48 can open, allowing more flow through the flow regulator valve 48 and back into the inner canister. When pressure within the circuit decreases (due to lower RVR), the flow regulator valve 48 can close such that more perfusates passes through the kidney. The flow regulator valve 48 can ensure that pressure within the circuit remains below the perfusion pressure limit, or upper threshold. In some examples, the upper threshold is 65 mmHg. In some examples, the upper threshold is between 50 and 80 mmHg. In some examples, the upper threshold is between 30 and 100 mmHg.

The flow regulator valve 48 can include a ball 1350 and a spring 1352 in a housing 1354. The ball 1350, the spring 1352, and/or the housing can be metal, for example stainless steel. When pressurized in the flow direction F, the spring 1352 can compress and allow fluid to pass around the ball 1350. When pressure in the flow direction F decreases, the spring 1352 can extend and the ball 1350 can block flow. The properties of the flow regulator valve 48 can be engineered and/or adjusted to have a specific cracking pressure, or the pressure at which the ball is pushed back to allow the fluid to flow through. The flow through the flow regulator valve 48 can be variable as opposed to binary. Advantageously, the flow regulator valve 48 can control flow in a manner directly proportional to the resistance of an artery without requiring active maintenance or software.

Figure 14:
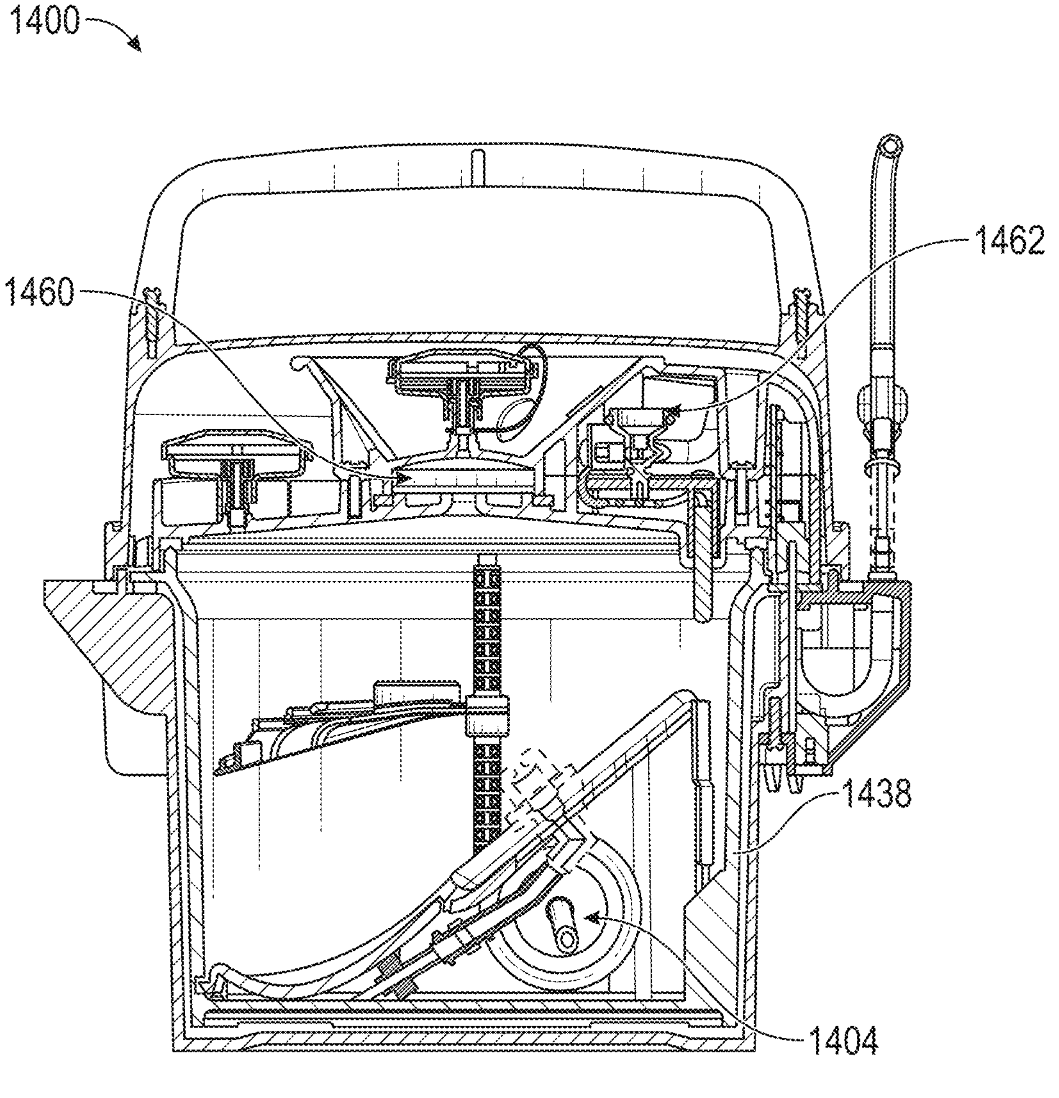
FIG. 14 shows a cross-sectional view of an example of an organ preservation apparatus with a canister bubble trap and a perfusion line bubble trap.

FIG. 14 shows a cross-sectional view of an example of an organ preservation apparatus 1400 with a canister bubble trap 1460 and a perfusion line bubble trap 1462.

The organ preservation apparatus 1400 can be similar to the apparatus 10 of FIG. 1A-C. The canister 1438 can include a filter 1404.

The apparatus 1400 can include a canister bubble trap 1460. The canister bubble trap 1460 can be integrated in the inner lid 1440. For example, the canister bubble trap 1460 can be integrated in the center of the inner lid 1440. The canister bubble trap 1460 can prevent air from entering and/or remaining in the canister 1438.

The apparatus 1400 can include a perfusion line bubble trap 1462. The perfusion line bubble trap 1462 can be integrated in the inner lid 1440. For example, the perfusion line bubble trap 1462 can be integrated in the perfusion circuit as fluid is pumped to and/or from the canister 1438. The perfusion line bubble trap 1462 can prevent air from entering and/or remaining in the perfusion circuit.

Figure 15:
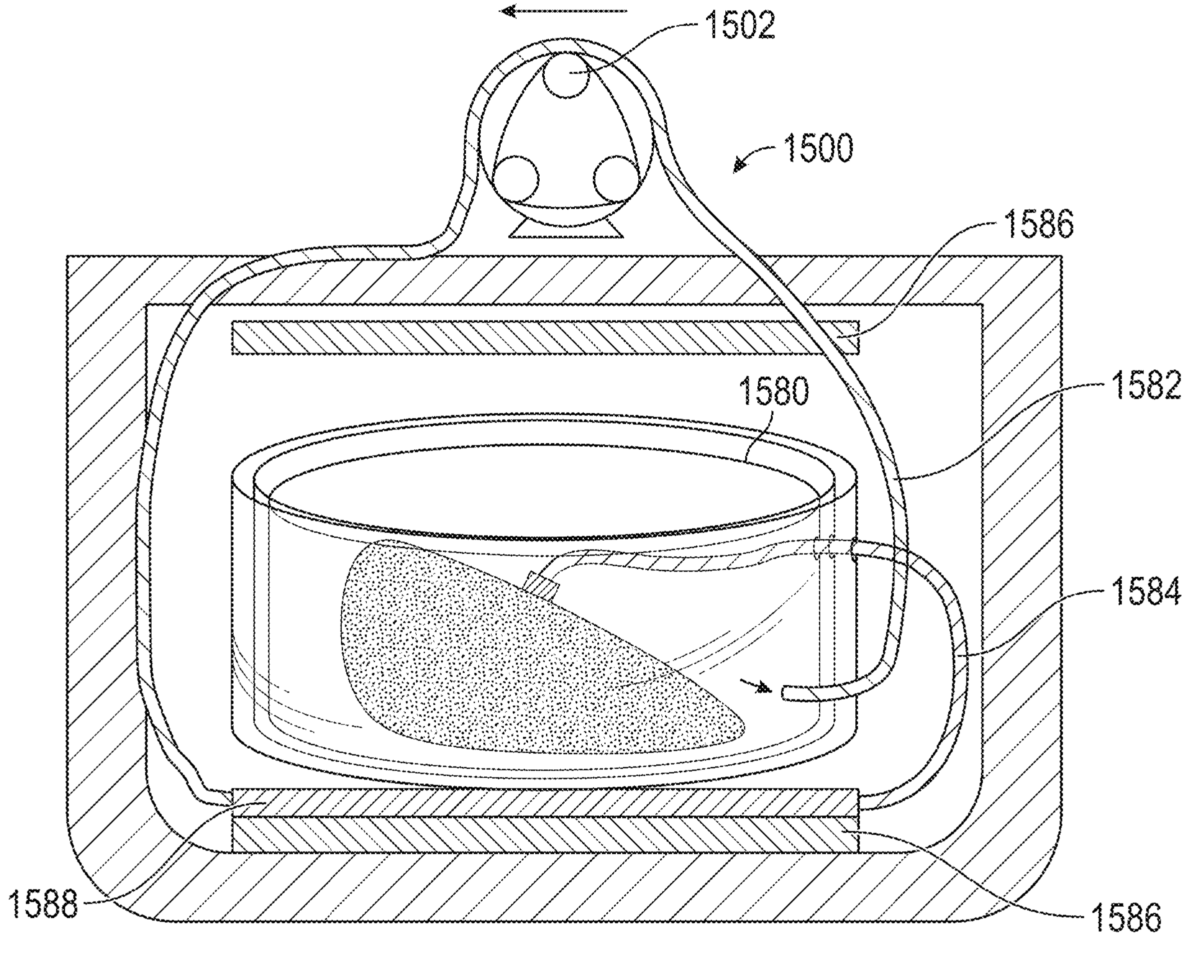
FIG. 15 shows an example of an organ preservation apparatus for preserving an organ.

FIG. 15 shows an example of an organ preservation apparatus 1500 for preserving an organ.

The organ preservation apparatus 1500 can include any and/or all of the features of the apparatus 10 or the apparatus 1400 as described with respect to FIGS. 1A-C and 14.

The apparatus 1500 can be used to ensure or promote homogenous cooling of a donor organ. The apparatus 1500 can circulate cold preservation fluid in a manner that efficiently and effectively cools the organ from within the organ.

In some examples, the organ can be a liver. Because the liver has a larger mass than certain other organs, the liver can be more difficult to cool evenly. In some examples, the organ can be a kidney, a heart, a lung, and/or a pancreas. The organ or biological sample T can be contained in nested containers 1580. In some examples, the biological sample T can be contained in a bag, a container, or nested bags.

Preservation from inside the nested containers 1580 can flow through the first channel 1582. The pump 1502 can pump the fluid from inside the nested containers 1580 along the first channel 1582 to a temperature maintenance mechanism 1588, or heat exchanger. Due to the proximity of the temperature maintenance mechanism 1588 to the cooling media 1586, the temperature maintenance mechanism 1588 can reduce the temperature of the preservation fluid. In some examples, the temperature maintenance mechanism 1588 can include an active cooling mechanism, for example a refrigerator or an electronic cooler. The fluid can flow from the temperature maintenance mechanism 1588 through the second channel 1584 to a vessel of the organ. For example, the second channel 1584 can connect to a portal vein and/or a hepatic artery of a liver. In some examples, the second channel 1584 can connect to a renal artery of a kidney. The apparatus 1500 can also include cooling media 1586 disposed on or near the lid of the canister.

In some examples, the apparatus 1500 can cool a liver to an approximately homogenous temperature in less than 30 minutes. In some examples, the apparatus 1500 can cool a liver to an approximately homogenous temperature in less than between 15 and 60 minutes. In some examples, the apparatus 1500 can store a liver for approximately 15 hours. In some examples, the apparatus 1500 can store a liver for approximately 5-30 hours.

The cannula coupling the vessel or vessels of the organ with the first channel 1582 can include sensors. For example, the cannula can include a temperature sensor and/or a pressure sensor. The sensors can determine perfusate temperature, portal vein pressure, and/or hepatic artery pressure. The cannula can include a check valve to provide pressure relief to the organ.

Figures 16, 17:
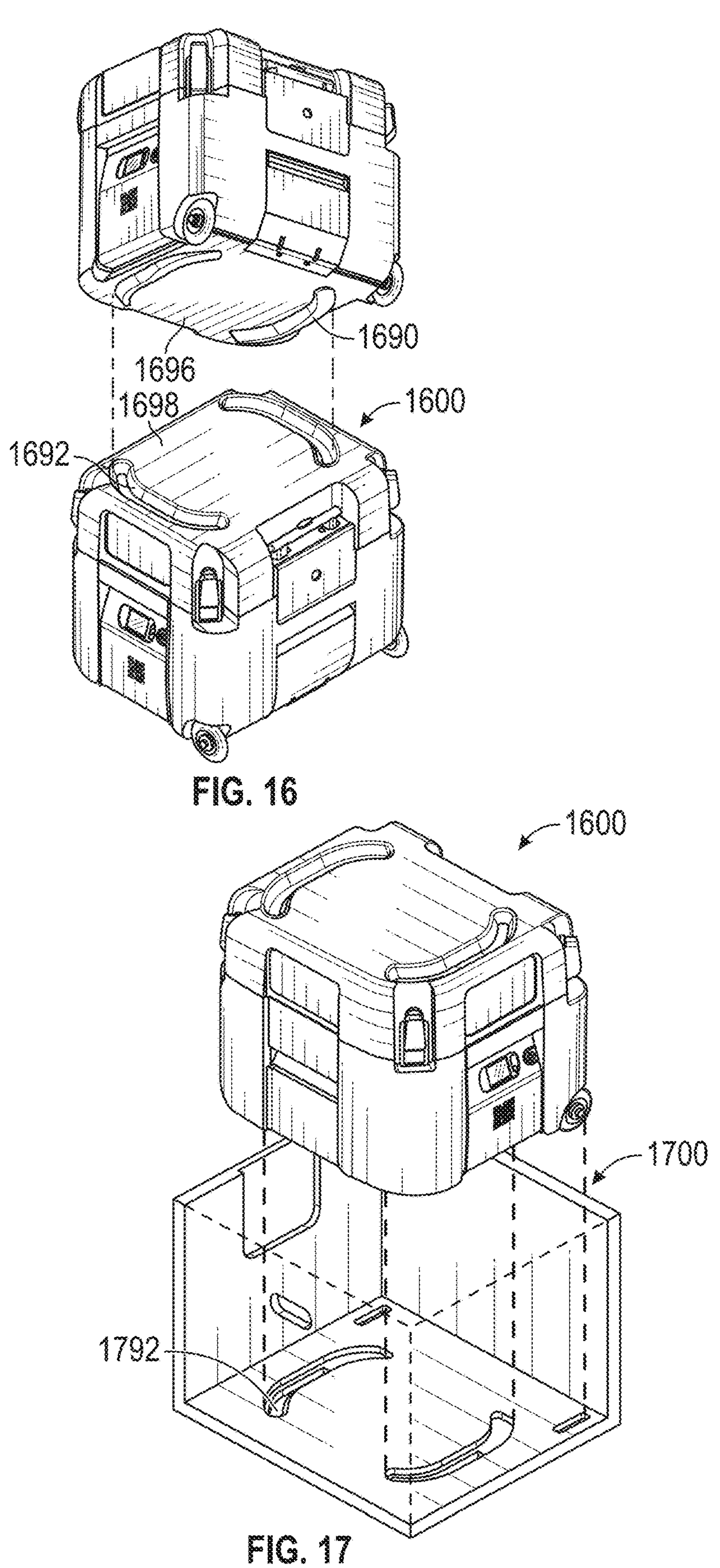
FIG. 16 shows an example of transporters aligned for stacking.
FIG. 17 shows an example of a transporter aligned for placement in a package.

FIG. 16 shows an example of transporters 1600 aligned for stacking.

The transporters 1600 can be similar to the transporter 400 described with respect to FIGS. 4A-4B.

The transporters 1600 can be stacked such that protrusions 1690 on the bottom of the transporter 1600 are aligned with and stacked on top of recesses 1692 on the top of a transporter. In some examples, the protrusions 1690 and/or the recesses 1692 can be C-shaped, curved, semicircular, or parenthesis shaped. In some examples, the protrusions 1690 and/or the recesses 1692 can be linear, rectangular, or another shape. In some examples, transporters 1600 can be stacked such that the transporters 1600 are facing the same direction. In some examples, transporters 1600 can be stacked such that the transporters 1600 are facing opposite directions. Advantageously, in organs received in donors who have undergone cardiac death or brain death, two kidneys can be transported together with the transporters 1600 in the stacked formation. This can allow for simultaneous and efficient monitoring of individual organ statistics such as renal pressure and/or temperature.

Stacking transporters 1600 can allow multiple devices to be transported efficiently and securely, which can optimize space during transportation and shipping. Each transporter 1600 can include a wide wheelbase to improve stability and maneuverability of the device. The transporters 1600 can include indents 1696 on or near the front of the transporter 1600. These indents can cradle the telescoping handle arms of another transporter 1600 to secure the transporters 1600 together when stacked while facing opposite directions. Advantageously, this allows the transporters 1600 to be tilted backwards and rolled together on the wheels of the lower transporter 1600 to enhance mobility and ease of handling during transport. In some examples, each side of the transporter 1600 can include ergonomic areas to handle and maneuver the device, for example indentations on the four faces of the transporter 1600.

Each transporter 1600 can include a pocket 1698 on the top of the transporter 1600 to contain paperwork. For example, the pocket 1698 can be a clear, plastic pocket. In some examples, the pocket 1698 can be used to store OPO paperwork.

FIG. 17 shows an example of a transporter 1600 aligned for placement in a package 1700.

The transporter 1600 can have a specialized package 1700 to contain the transporter 1600. The specialized package 1700 can include recesses 1792 configured to receive the protrusions 1990 of the transporter 1600. This can simplify the process of removing and replacing the device from the packaging.

Figure 18A:
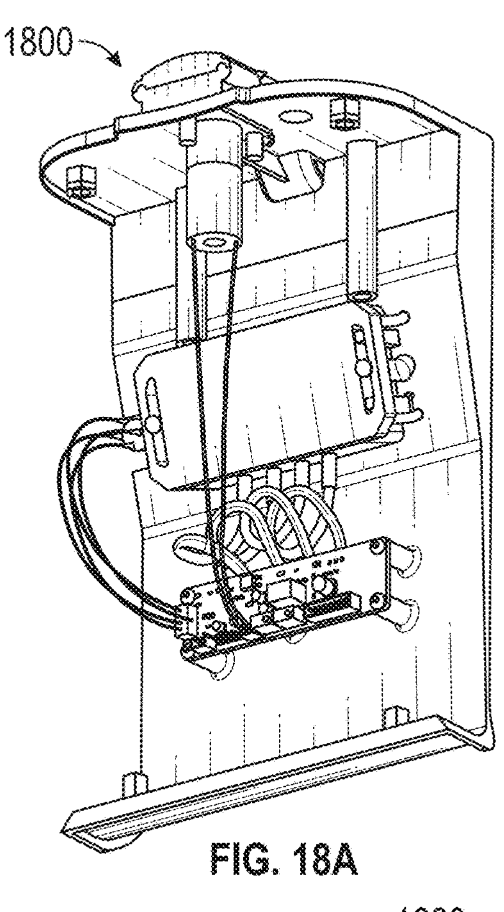
FIG. 18A shows an example of a removable electronics panel.
Figure 18B:
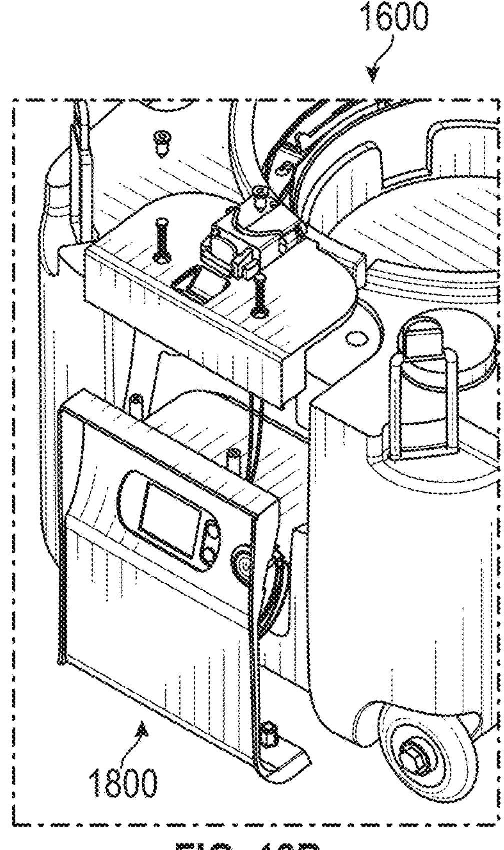
FIG. 18B shows the example of the electronics panel of FIG. 18A being positioned on the transporter.

FIG. 18A shows an example of a removable electronics panel 1800. FIG. 18B shows the example of the electronics panel of FIG. 18A being positioned on the transporter 1600.

The electronics panel 1800 can be removed from the transporter 1600. The electronics panel 1800 can include a display and a processor. The electronics panel 1800 can be accessible for ease of maintenance and repair.

In some examples, the display can indicate organ perfusion status in real-time, organ ID number, blood type, cross-clamp and total infusion time, perfusate temperature, hepatic and portal flow, renal pressure, pressure, and/or total flow.

EXAMPLES

Additional systems and methods are disclosed in the examples below, which should not be viewed as limiting the invention in any way.

Example 1. A system for hypothermic transport of an organ, for example a kidney, a lung, a heart, or a liver, comprising: a transport container configured to receive an organ, the transport container configured to be at least partially filled with preservation fluid, the transport container comprising: a fluid circuit comprising: an inlet configured to be in communication with the preservation fluid in the transport container; a flow regulator valve in fluid communication with the inlet, the flow regulator valve configured to release the preservation fluid from the fluid circuit into the transport container at a rate based on vessel resistance of the organ; and an outlet in fluid communication with the flow regulator valve and the organ; and a pump configured to pump the preservation fluid from the inlet to the organ, the pump configured to operate independently of vessel resistance.

Example 2. The system of Example 1, wherein the transport container further comprises an organ rest configured to support the organ.

Example 3. The system of Example 2, further comprising an organ adapter configured to seal a vessel of the organ, the organ adapter adjustable along a groove of the organ rest.

Example 4. The system of any one of Examples 1-3, further comprising a pressure dampener, wherein the pressure dampener is configured to reduce pulsation in the fluid circuit caused by the pump.

Example 5. The system of any one of Examples 1-4, wherein the pump is a peristaltic pump.

Example 6. The system of any one of Examples 1-5, wherein the flow regulator valve releases the preservation fluid from the fluid circuit into the transport container at a higher rate when vessel resistance is higher.

Example 7. The system of any one of Examples 1-6, wherein the transport container further comprises: a plurality of posts; and an organ retainer adjustably couplable to the plurality of posts.

Example 8. The system of any one of Examples 1-7, wherein the transport container further comprises a one-way valve in fluid communication with the fluid circuit, the one-way valve configured to take in preservation fluid from the transport container when fluid is drawn out of the fluid circuit.

Example 9. The system of any one of Examples 1-8, wherein the transport container further comprises a temperature sensor.

Example 10. The system of any one of Examples 1-9, further comprising a lid comprising a fill port and a vent port.

Example 11. The system of Example 10, further comprising an accumulation chamber configured to seal to at least one of the fill port and the vent port, the accumulation chamber comprising a balloon configured to expand when the preservation fluid expands and contract when the preservation fluid contracts.

Example 12. The system of Example 3, wherein the organ adapter comprises: a cannula comprising a barb, the cannula configured to seal to the vessel of the organ; and a cannula receiver configured to couple with the barb.

Example 13. A method for hypothermic transport of an organ, for example a kidney, a lung, a heart, or a liver, the method comprising: placing an organ in a transport container, the transport container comprising an organ adapter; sealing the organ adapter to a vessel of the organ; placing a lid on the transport container; filling the transport container at least partially with preservation fluid through a fill port in the lid; and activating a pump, the pump configured to pump the preservation fluid from the transport container to a flow regulator valve and the organ adapter, the flow regulator valve configured to release the preservation fluid into the transport container at a rate based on vessel resistance of the organ, and the pump configured to operate independently of vessel resistance.

Example 14. The method of Example 13, further comprising placing the organ on an organ rest.

Example 15. The method of Example 14, further comprising adjusting the organ adapter along a groove of the organ rest.

Example 16. The method of any one of Examples 13-15, further comprising attaching an organ retainer to a plurality posts in the transport container such that the organ retainer secures the organ.

Example 17. The method of any one of Examples 13-16, further comprising sealing an accumulation chamber to at least one of the fill port or a vent port on the lid.

Example 18. A system for hypothermic transport of an organ, for example a kidney, a lung, a heart, or a liver, comprising: a transport container configured to receive an organ, the transport container configured to be at least partially filled with preservation fluid; a pump configured to pump the preservation fluid from the transport container to the organ in a fluid circuit, the pump configured to operate independently of vessel resistance; and a flow regulator valve in fluid communication with the fluid circuit, the flow regulator valve configured to release the preservation fluid from the fluid circuit into the transport container at a rate based on vessel resistance of the organ.

Example 19. The system of Example 18, wherein the transport container further comprises an organ rest configured to support the organ.

Example 20. The system of Example 19, further comprising an organ adapter configured to seal a vessel of the organ, the organ adapter adjustable along a groove of the organ rest.

Example 21. The system of any one of Examples 18-20, further comprising a pressure dampener, wherein the pressure dampener is configured to reduce pulsation caused by the pump.

Example 22. The system of any one of Examples 18-21, wherein the pump is a peristaltic pump.

Example 23. The system of any one of Examples 18-22, wherein the flow regulator valve releases the preservation fluid from the fluid circuit into the transport container at a higher rate when vessel resistance is higher.

Example 24. The system of any one of Examples 18-23, wherein the transport container further comprises: a plurality of posts; and an organ retainer adjustably couplable to the plurality of posts.

Example 25. The system of any one of Examples 18-24, wherein the transport container further comprises a one-way valve in fluid communication with the fluid circuit, the one-way valve configured to take in preservation fluid from the transport container when fluid is drawn out of the fluid circuit.

Example 26. The system of any one of Examples 18-25, wherein the transport container further comprises a temperature sensor.

Example 27. The system of any one of Examples 18-26, further comprising a lid comprising a fill port and a vent port.

Example 28. The system of Example 27, further comprising an accumulation chamber configured to seal to at least one of the fill port and the vent port, the accumulation chamber comprising a balloon configured to expand when the preservation fluid expands and contract when the preservation fluid contracts.

Example 29. The system of Example 20, wherein the organ adapter comprises: a cannula comprising a barb, the cannula configured to seal to the vessel of the organ; and a cannula receiver configured to couple with the barb.

Example 30. A system for hypothermic transport of an organ, for example a kidney, a lung, a heart, or a liver, comprising: a canister configured to contain an organ and preservation fluid; an inner lid configured to couple with the canister; an outer canister configured to couple with the inner lid, the outer canister comprising a tube; and a pump configured to pump the preservation fluid in the tube such that the preservation fluid flows from the canister to the inner lid, from the inner lid to the outer canister, from the outer canister to the tube, from the tube to the outer canister, from the outer canister to the inner lid, from the inner lid to the organ, and from the organ to the canister.

Example 31. A system for hypothermic transport of an organ, for example a kidney, a lung, a heart, or a liver, comprising: a canister configured to receive an organ, the canister containing preservation fluid; a port between the canister and an environment; and an accumulation chamber configured to seal to the port, the accumulation chamber comprising a balloon configured to expand when the preservation fluid expands and contract when the preservation fluid contracts.

Example 32. A method for hypothermic transport of an organ, for example a kidney, a lung, a heart, or a liver, the method comprising: placing an organ in a canister; filling the canister with preservation fluid through a fill port; venting the canister of fluid through a vent port; and attaching an accumulation chamber on at least one of the fill port or the vent port, the accumulation chamber comprising a balloon configured to expand when the preservation fluid expands and contract when the preservation fluid contracts.

Example 33. A system for hypothermic transport of an organ, for example a kidney, a lung, a heart, or a liver, comprising: a canister configured to receive an organ, the canister comprising: an organ rest configured to support the organ; and a plurality of posts; and an organ retainer adjustably couplable to the plurality of posts.

Example 34. A method for hypothermic transport of an organ, for example a kidney, a lung, a heart, or a liver, the method comprising: placing an organ in a canister, the canister comprising an organ rest configured to support the organ and a plurality of posts; and coupling an organ retainer to the plurality of posts at a position such that the organ retainer contacts the organ.

Example 35. A system for hypothermic transport of an organ, for example a kidney, a lung, a heart, or a liver, comprising: a canister configured to receive an organ; an organ rest inside the canister configured to support the organ, the organ rest comprising a groove; and an organ adapter configured to seal to a vessel of the organ, the organ adapter movable along the groove.

Example 36. The system of Example 35, wherein the organ adapter comprises: a cannula configured to seal to the vessel of the organ; and a cannula receiver on the organ rest configured to couple with the cannula.

Example 37. A method for hypothermic transport of an organ, for example a kidney, a lung, a heart, or a liver, the method comprising: placing an organ in a canister on an organ rest, the organ rest comprising a groove; sealing an organ adapter to a vessel of the organ; moving the organ adapter along the groove; and locking the organ adapter in place such that a vessel artery of the organ is under tension.

Example 38. The method of Example 37, wherein sealing the organ adapter to the vessel of the organ comprises:

sealing the vessel of the organ with a cannula; and coupling the cannula to a cannula receiver on the organ rest.

Example 39. A system for hypothermic transport of an organ, for example a kidney, a lung, a heart, or a liver, comprising: a transport container configured to receive an organ, the transport container configured to be at least partially filled with preservation fluid, the transport container comprising: a fluid circuit comprising: an inlet configured to be in communication with the preservation fluid in the transport container; a heat exchanger in fluid communication with the inlet, the heat exchanger configured to cool the preservation fluid in the fluid circuit; and an outlet in fluid communication with the heat exchanger and a vessel of the organ; and a pump configured to pump the preservation fluid from the inlet to the heat exchanger and from the heat exchanger to the organ.

Example 40. The system of Example 39, wherein the transport container further comprises an organ rest configured to support the organ.

Example 41. The system of Example 40, further comprising an organ adapter configured to seal a vessel of the organ, the organ adapter adjustable along a groove of the organ rest.

Example 42. The system of any one of Examples 39-41, further comprising a pressure dampener, wherein the pressure dampener is configured to reduce pulsation in the fluid circuit caused by the pump.

Example 43. The system of any one of Examples 39-42, wherein the pump is a peristaltic pump.

Example 44. The system of any one of Examples 1-12, further comprising a bubble trap integrated in a lid of the transport container.

Example 45. The system of any one of Examples 1-12, further comprising a bubble trap integrated in the fluid circuit.

Example 46. An apparatus substantially as shown and/or described.

Example 47. A method substantially as shown and/or described.

Example 48. A system substantially as shown and/or described.

In various embodiments, cooling blocks may include eutectic cooling media or other phase change material (PCM) such as savENRG packs with PCM HS01P material commercially available from RGEES, LLC or Akuratemp, LLC (Arden, NC). Exemplary PCM specifications including a freezing temperature of 0° C.+/0.5° C., a melting temperature of 1° C.+/0.75° C., latent heat of 310 J/g+/10 J/g, and density of 0.95 gram/ml+/0.05 gram/ml. Pouch dimensions may vary depending on application specifics such as tissue to be transported and the internal dimensions of the transport container and external dimensions of the tissue storage device, chamber, or canister. PCM may be included in pouches approximately 10 inches by 6 inches having approximately 230 g of PCM therein. Pouches may be approximately 8.5 mm thick and weigh about 235 g to 247 g. In some embodiments, pouches may be approximately 6.25 inches by 7.75 inches with a thickness of less than about 8.5 mm and a weight of between about 193 g and about 201 g. Other exemplary dimensions may include about 6.25 inches by about 10 inches. Pouches may be stacked or layered, for example in groups of 3 or 4 to increase the total thickness and amount of PCM. In certain embodiments, PCM containing pouches may be joined side to side to form a band of coupled PCM pouches. Such a band may be readily manipulated to wrap around the circumference of a cylindrical storage container and may have dimensions of about 6 inches by about 26 inches consisting of approximately 8 individual pouches joined together in the band.

A variety of preservation solutions can be used with the disclosed systems, devices, and methods. This includes approved preservation solutions, such as Histidine Tryptophan Ketoglutarate (HTK) (e.g., HTK Custodial™) and Celsior™ solutions for the preservation of hearts and cardiac tissues, and University of Wisconsin Solution (Viaspan™) and MPS 1 for the preservation of kidney and kidney tissues. Other preservation solutions, including non approved solutions, and off label applications of approved solutions can be used with the devices described herein. Various preservation solutions can be used, including Collins, EuroCollins, phosphate buffered sucrose (PBS), University of Wisconsin (UW) (e.g., Belzer Machine Preservation Solution (MPS)), histidine tryptophan ketoglutarate (HTK), hypertonic citrate, hydroxyethyl starch, and Celsior™. Additional details of these solutions can be found at t'Hart et al. "New Solutions in Organ Preservation," Transplantation Reviews 2006, vol. 16, pp. 131 141 (2006).

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the principles and features disclosed herein. Various combinations and subcombinations of the various features described herein are possible. Certain embodiments are encompassed in the claim set listed below.

Although this disclosure describes certain embodiments, it will be understood by those skilled in the art that many aspects of the methods and devices shown and described in the present disclosure may be differently combined and/or modified to form still further embodiments or acceptable examples. All such modifications and variations are intended to be included herein within the scope of this disclosure. Indeed, a wide variety of designs and approaches are possible and are within the scope of this disclosure. No feature, structure, or step disclosed herein is essential or indispensable. Moreover, while illustrative embodiments have been described herein, the scope of any and all embodiments having equivalent elements, modifications, omissions, combinations (e.g., of aspects across various embodiments), substitutions, adaptations and/or alterations as would be appreciated by those in the art based on the present disclosure. While certain embodiments have been described, these embodiments have been presented by way of example only, and are not intended to limit the scope of protection.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A system for preservation of a biological sample comprising:

a transport container configured to contain a biological sample;

a pump configured to pump preservation fluid from the transport container to an inlet of a fluid circuit;

a flow regulator valve in fluid communication with the inlet, the flow regulator valve configured to regulate a flow rate into the biological sample based on a biological sample parameter, wherein the flow regulator valve is configured to release fluid into the transport container at a rate based on the biological sample parameter; and a biological sample adapter in fluid communication with the inlet of the fluid circuit and configured to couple with the biological sample, wherein the biological sample parameter comprises at least one of vessel resistance, biological sample temperature, or flow rate through the biological sample, wherein the fluid circuit comprises fluid in the transport container and fluid flowing from the inlet to the biological sample adapter when the biological sample is contained in the transport container and coupled with the biological sample adapter, and wherein the fluid circuit is configured to form a closed fluid system when the biological sample is contained in the transport container and coupled with the biological sample adapter.

2. The system of claim 1, further comprising a biological sample rest configured to support the biological sample.

3. The system of claim 2, wherein the biological sample rest further comprises a cannula receiver, the cannula receiver configured to receive the biological sample adapter.

4. The system of claim 3, wherein the biological sample rest further comprises a groove, wherein the cannula receiver is adjustable along the groove.

5. The system of claim 4, further comprising a locking mechanism configured to lock the biological sample adapter in place along the groove such that a vessel of the biological sample is under tension.

6. The system of claim 1, further comprising a biological sample retainer configured to attach to a plurality of posts in the transport container such that the biological sample retainer secures the biological sample.

7. The system of claim 1, wherein the transport container further comprises a vent port configured to vent fluid from the transport container.

8. The system of claim 7, further comprising an accumulation chamber configured to be attached to at least one of a fill port or the vent port, the accumulation chamber comprising a flexible membrane configured to expand when the preservation fluid expands and contract when the preservation fluid contracts.

9. The system of claim 1, wherein the flow regulator valve is configured to maintain the flow rate into the biological sample to preserve the biological sample for greater than 5 hours without adjusting parameters of the pump.

10. The system of claim 1, further comprising a phase change material positioned on an outer lid sealed to the transport container.

11. The system of claim 1, further comprising a pressure dampener configured to reduce pulsation in the fluid circuit.

12. The system of claim 1, further comprising a pressure sensor configured to measure a pressure in the fluid circuit.

13. The system of claim 12, further comprising a display configured to display the pressure in the fluid circuit.

14. The system of claim 1, further comprising a temperature sensor configured to measure a temperature in the fluid circuit.

15. The system of claim 14, further comprising a display configured to display the temperature in the fluid circuit on a display of the transport container.

16. A system for preservation of a biological sample comprising:

a transport container configured to contain a biological sample;

a pump configured to pump preservation fluid through a fluid circuit to a flow regulator valve, the flow regulator valve configured to regulate a flow rate into the biological sample based on a biological sample parameter, wherein the flow regulator valve is configured to release fluid into the transport container at a rate based on the biological sample parameter; and a biological sample adapter in fluid communication with the flow regulator valve and configured to couple with the biological sample, wherein the biological sample parameter comprises at least one of vessel resistance, biological sample temperature, flow rate through the biological sample, or organ pressure, wherein the fluid circuit comprises fluid in the transport container and fluid flowing from the transport container to the biological sample adapter when the biological sample is contained in the transport container and coupled with the biological sample adapter, and wherein the transport container and the fluid circuit are configured to form a closed fluid system when the biological sample is contained in the transport container and coupled with the biological sample adapter.

17. The system of claim 16, wherein the transport container further comprises a vent port configured to vent fluid from the transport container.

18. The system of claim 17, further comprising an accumulation chamber configured to be attached to at least one of a fill port or the vent port, the accumulation chamber comprising a flexible membrane configured to expand when the preservation fluid expands and contract when the preservation fluid contracts.

19. The system of claim 16, further comprising a phase change material positioned on an outer lid sealed to the transport container.

20. The system of claim 16, further comprising a pressure dampener configured to reduce pulsation in the fluid circuit.

* * * * *